US011911135B2

(12) United States Patent
Vecchio

(10) Patent No.: US 11,911,135 B2
(45) Date of Patent: Feb. 27, 2024

(54) IMPLANTABLE MEDICAL DEVICE WITH ADJUSTABLE BLOOD FLOW

(71) Applicant: W. L. Gore & Associates, Inc., Newark, DE (US)

(72) Inventor: Christopher J. Vecchio, Philidelphia, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 1004 days.

(21) Appl. No.: 16/724,788

(22) Filed: Dec. 23, 2019

(65) Prior Publication Data

US 2020/0197178 A1    Jun. 25, 2020

Related U.S. Application Data

(60) Provisional application No. 62/901,105, filed on Sep. 16, 2019, provisional application No. 62/894,260, (Continued)

(51) Int. Cl.
*A61F 2/24* (2006.01)
*A61B 5/00* (2006.01)
(Continued)

(52) U.S. Cl.
CPC ........ *A61B 5/02055* (2013.01); *A61B 5/0031* (2013.01); *A61B 5/0205* (2013.01);
(Continued)

(58) Field of Classification Search
CPC ...... A61B 17/12022; A61B 2560/0219; A61B 5/0031; A61B 5/0205; A61B 5/02055;
(Continued)

(56) References Cited

U.S. PATENT DOCUMENTS 5,276,276 A    1/1994 Gunn
5,334,217 A    8/1994 Das
(Continued)

FOREIGN PATENT DOCUMENTS

CN    104414692 A     3/2015
EP     1264572 A1    12/2002
(Continued)

OTHER PUBLICATIONS

Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, pp. 40-48.
(Continued)

*Primary Examiner* — Kai H Weng

(57) ABSTRACT

An implantable medical device is disclosed, in which the implantable medical device includes a fluid shunt extending through a wall separating a first cavity and a second cavity within the heart. The fluid shunt includes a first portion adapted to extend into the first cavity within the heart, a second portion adapted to extend into the second cavity within the heart, and an intermediate portion interconnecting the first and second portions. The fluid shunt having a lumen extending between the first and second portions that is adapted to fluidly couple the first and second cavities within the heart. The implantable medical device also includes an occlusion assembly associated with the fluid shunt and adapted to selectively occlude flow through the lumen of the fluid shunt, where the occlusion assembly is activated to adjust flow through the lumen of the fluid shunt, The implantable medical device further includes at least one sensor assembly associated with the first portion of the fluid shunt such that the at least one sensor assembly senses one or more physiologic parameters in the first cavity.

19 Claims, 15 Drawing Sheets

Related U.S. Application Data filed on Aug. 30, 2019, provisional application No. 62/845,386, filed on May 9, 2019, provisional application No. 62/783,935, filed on Dec. 21, 2018, provisional application No. 62/783,902, filed on Dec. 21, 2018.

(51) Int. Cl.

| | | |
|---|---|---|
| *A61B 5/0205* | (2006.01) | |
| *A61B 5/07* | (2006.01) | |
| *A61B 5/145* | (2006.01) | |
| *A61B 5/1455* | (2006.01) | |
| *A61B 5/20* | (2006.01) | |
| *A61L 31/10* | (2006.01) | |
| *A61M 27/00* | (2006.01) | |
| *A61B 5/0215* | (2006.01) | |
| *A61B 17/12* | (2006.01) | |
| *A61L 31/00* | (2006.01) | |
| *A61L 31/08* | (2006.01) | |

(52) U.S. Cl.
CPC .......... *A61B 5/076* (2013.01); *A61B 5/14542* (2013.01); *A61B 5/14552* (2013.01); *A61B 5/201* (2013.01); *A61B 5/4839* (2013.01); *A61B 5/486* (2013.01); *A61B 5/6847* (2013.01); *A61B 5/7275* (2013.01); *A61B 5/742* (2013.01); *A61F 2/2487* (2013.01); *A61L 31/10* (2013.01); *A61M 27/002* (2013.01); *A61B 5/0215* (2013.01); *A61B 5/02158* (2013.01); *A61B 17/12022* (2013.01); *A61B 2560/0219* (2013.01); *A61F 2250/0001* (2013.01); *A61F 2250/0002* (2013.01); *A61F 2250/0069* (2013.01); *A61F 2250/0093* (2013.01); *A61L 31/00* (2013.01); *A61L 31/08* (2013.01); *A61L 2300/236* (2013.01); *A61L 2300/42* (2013.01); *A61M 2205/04* (2013.01); *A61M 2205/3303* (2013.01); *A61M 2205/3331* (2013.01); *A61M 2205/3507* (2013.01)

(58) Field of Classification Search
CPC ... A61B 5/0215; A61B 5/02158; A61B 5/076; A61B 5/14542; A61B 5/14552; A61B 5/201; A61B 5/4839; A61B 5/486; A61B 5/6847; A61B 5/7275; A61B 5/742; A61F 2/2487; A61F 2250/0001; A61F 2250/0002; A61F 2250/0069; A61F 2250/0093; A61M 2205/04; A61M 2205/3303; A61M 2205/3331; A61M 2205/3507; A61M 27/002

See application file for complete search history.

(56) References Cited

U.S. PATENT DOCUMENTS

| | | |
|---|---|---|
| 5,683,411 A | 11/1997 | Kavteladze et al. |
| 5,944,738 A | 8/1999 | Amplatz et al. |
| 6,042,602 A | 3/2000 | Wells |
| 6,042,605 A | 3/2000 | Martin et al. |
| 6,077,291 A | 6/2000 | Das |
| 6,080,182 A | 6/2000 | Shaw et al. |
| 6,461,665 B1 | 10/2002 | Scholander |
| 6,911,037 B2 | 6/2005 | Gainor et al. |
| 6,926,670 B2 | 8/2005 | Rich et al. |
| 7,001,409 B2 | 2/2006 | Amplatz |
| 7,049,380 B1 | 5/2006 | Chang et al. |
| 7,236,821 B2 | 6/2007 | Cates et al. |
| 7,462,675 B2 | 12/2008 | Chang et al. |
| 7,871,659 B2 | 1/2011 | Cook et al. |
| 7,887,562 B2 | 2/2011 | Young et al. |
| 7,901,702 B2 | 3/2011 | Schwarz |
| 8,021,331 B2 | 9/2011 | Herweck et al. |
| 8,043,360 B2 | 10/2011 | McNamara et al. |
| 8,048,440 B2 | 11/2011 | Chang et al. |
| 8,480,707 B2 | 7/2013 | Pavcnik et al. |
| 8,545,525 B2 | 10/2013 | Surti et al. |
| 8,696,693 B2 | 4/2014 | Najafi et al. |
| 8,715,300 B2 | 5/2014 | Najafi et al. |
| 8,728,103 B2 | 5/2014 | Surti et al. |
| 9,241,695 B2 | 1/2016 | Peavey et al. |
| 9,314,556 B2 | 4/2016 | Tuseth |
| 9,358,371 B2 | 6/2016 | McNamara et al. |
| 9,399,085 B2 | 7/2016 | Cleek et al. |
| 9,456,812 B2 | 10/2016 | Finch et al. |
| 9,545,300 B2 | 1/2017 | Cully et al. |
| 9,554,786 B2 | 1/2017 | Carley et al. |
| 9,629,715 B2 | 4/2017 | Nitzan et al. |
| 9,636,094 B2 | 5/2017 | Aurilia et al. |
| 9,649,481 B2 | 5/2017 | Sadanand |
| 9,681,948 B2 | 6/2017 | Levi et al. |
| 9,757,107 B2 | 9/2017 | McNamara et al. |
| 9,775,591 B2 | 10/2017 | Delgado et al. |
| 9,861,346 B2 | 1/2018 | Callaghan |
| 9,878,162 B2 | 1/2018 | Mika et al. |
| 9,949,728 B2 | 4/2018 | Cahill |
| 11,540,731 B2 | 1/2023 | Minor et al. |
| 2002/0077555 A1 | 6/2002 | Schwartz |
| 2002/0077556 A1 | 6/2002 | Schwartz |
| 2002/0169475 A1 | 11/2002 | Gainor et al. |
| 2002/0173742 A1 | 11/2002 | Keren et al. |
| 2003/0055344 A1 | 3/2003 | Eigler et al. |
| 2003/0139819 A1 | 7/2003 | Beer et al. |
| 2004/0063805 A1 | 4/2004 | Pacetti et al. |
| 2005/0038351 A1 | 2/2005 | Starobin et al. |
| 2005/0148925 A1 | 7/2005 | Rottenberg et al. |
| 2006/0008500 A1 | 1/2006 | Chavan et al. |
| 2006/0116590 A1 | 6/2006 | Fayram et al. |
| 2006/0198866 A1 | 9/2006 | Chang et al. |
| 2006/0271116 A1 | 11/2006 | Stahmann et al. |
| 2007/0032734 A1 | 2/2007 | Najafi et al. |
| 2007/0118039 A1 | 5/2007 | Bodecker et al. |
| 2007/0282430 A1 | 12/2007 | Thommen et al. |
| 2008/0221551 A1 | 9/2008 | Goodson et al. |
| 2008/0249562 A1 | 10/2008 | Cahill |
| 2008/0262518 A1 | 10/2008 | Freudenthal |
| 2009/0024042 A1 | 1/2009 | Nunez et al. |
| 2009/0030331 A1 | 1/2009 | Hochareon et al. |
| 2009/0221923 A1 | 9/2009 | Jemura et al. |
| 2010/0049313 A1 | 2/2010 | Alon et al. |
| 2010/0069778 A1 | 3/2010 | Bornzin et al. |
| 2010/0094401 A1 | 4/2010 | Kolbel et al. |
| 2011/0071623 A1 | 3/2011 | Finch et al. |
| 2011/0098767 A1 | 4/2011 | Sugimachi et al. |
| 2011/0295183 A1 | 12/2011 | Finch et al. |
| 2011/0295366 A1 | 12/2011 | Finch et al. |
| 2011/0303229 A1 | 12/2011 | Najafi et al. |
| 2012/0136385 A1 | 5/2012 | Cully |
| 2012/0265296 A1 | 10/2012 | McNamara et al. |
| 2013/0165967 A1 | 6/2013 | Amin et al. |
| 2013/0281988 A1 | 10/2013 | Magnin et al. |
| 2014/0012368 A1 | 1/2014 | Sugimoto et al. |
| 2014/0128795 A1 | 5/2014 | Keren et al. |
| 2014/0142617 A1 | 5/2014 | Larsen et al. |
| 2014/0207153 A1 | 7/2014 | Najafi et al. |
| 2014/0222040 A1 | 8/2014 | Park et al. |
| 2014/0228683 A1 | 8/2014 | Aoki et al. |
| 2014/0343670 A1 | 11/2014 | Bakis et al. |
| 2015/0039084 A1 | 2/2015 | Levi et al. |
| 2015/0142049 A1 | 5/2015 | Delgado et al. |
| 2015/0313599 A1 | 11/2015 | Johnson et al. |
| 2016/0045165 A1* | 2/2016 | Braido ................ A61B 5/6847 623/2.1 |
| 2016/0058452 A1 | 3/2016 | Brenneman et al. |
| 2016/0263299 A1 | 9/2016 | Xu et al. |
| 2017/0042705 A1 | 2/2017 | Cook et al. |
| 2017/0105711 A1 | 4/2017 | Masters |
| 2017/0106176 A1 | 4/2017 | Taft et al. |
| 2017/0172766 A1 | 6/2017 | Vong et al. |
| 2017/0196673 A1 | 7/2017 | Cully et al. |

(56) References Cited

U.S. PATENT DOCUMENTS

| | | |
|---|---|---|
| 2017/0281339 A1 | 10/2017 | Levi et al. |
| 2017/0319823 A1 | 11/2017 | Yacoby et al. |
| 2017/0358942 A1 | 12/2017 | Pugh et al. |
| 2018/0000580 A1 | 1/2018 | Wallace et al. |
| 2018/0008830 A1 | 1/2018 | Kaiser |
| 2018/0098772 A1 | 4/2018 | Goldshtein et al. |
| 2018/0126179 A1 | 5/2018 | Haasl et al. |
| 2018/0280667 A1 | 10/2018 | Keren |
| 2019/0130069 A1 | 5/2019 | Li et al. |
| 2019/0282178 A1 | 9/2019 | Volosin et al. |
| 2020/0038567 A1 | 2/2020 | Siess et al. |
| 2020/0085378 A1 | 3/2020 | Burnett et al. |
| 2020/0179663 A1 | 6/2020 | McDaniel et al. |
| 2020/0196876 A1 | 6/2020 | Minor et al. |
| 2020/0196943 A1 | 6/2020 | Minor et al. |
| 2020/0196944 A1 | 6/2020 | Minor et al. |
| 2021/0259839 A1 | 8/2021 | Cole et al. |
| 2021/0290214 A1 | 9/2021 | Cole et al. |

FOREIGN PATENT DOCUMENTS

| | | |
|---|---|---|
| EP | 2020248 A1 | 2/2009 |
| EP | 2637576 A1 | 9/2013 |
| GB | 1355373 A | 6/1974 |
| GB | 1506432 A | 4/1978 |
| GB | 1509023 A | 4/1978 |
| JP | 2003-061917 A | 3/2003 |
| JP | 2003-519542 A | 6/2003 |
| JP | 2006-528023 A | 12/2006 |
| JP | 2007-527742 A | 10/2007 |
| JP | 2008-545471 A | 12/2008 |
| JP | 2009-517137 A | 4/2009 |
| JP | 2010-505481 A | 2/2010 |
| JP | 2012-525210 A | 10/2012 |
| JP | 2013-517890 A | 5/2013 |
| JP | 2014-151049 A | 8/2014 |
| JP | 2016-538094 A | 12/2016 |
| JP | 2017-536857 A | 12/2017 |
| WO | 93/13712 A1 | 7/1993 |
| WO | 01/51123 A1 | 7/2001 |
| WO | 2004/091411 A2 | 10/2004 |
| WO | 2005/074367 A2 | 8/2005 |
| WO | 2006/054343 A1 | 5/2006 |
| WO | 2007/062299 A2 | 5/2007 |
| WO | 2008/040555 A2 | 4/2008 |
| WO | 2009/137755 A2 | 11/2009 |
| WO | 2010/129089 A2 | 11/2010 |
| WO | 2011/093941 A2 | 8/2011 |
| WO | 2012/091809 A1 | 7/2012 |
| WO | 2014/150106 A1 | 9/2014 |
| WO | 2015/109027 A2 | 7/2015 |
| WO | 2017/118738 A1 | 7/2017 |

OTHER PUBLICATIONS

Feldman et al., "Transcatheter Interatrial Shunt Device for the Treatment of Heart Failure Rationale and Design of the Randomized Trial to REDUCE Elevated Left Atrial Pressure in Heart Failure (Reduce LAP-HF I)", Circulation Heart failure, vol. 9, No. 7, 2016, pp. 1-10.

Gregg et al., "Interatrial Shunting for Heart Failure The V-Wave Shunt", Presentation at the Transcatheter Cardiovascular Therapeutics (TCT) Congress in Denver, Colorado, 2017, 18 pages.

International Preliminary Report on Patentability received for PCT Patent Application No. PCT/US2019/065610, dated Jun. 24, 2021, 9 pages.

International Preliminary Report on Patentability received for PCT Patent Application No. PCT/US2019/068275, dated Jul. 1, 2021, 11 pages.

International Preliminary Report on Patentability received for PCT Patent Application No. PCT/US2019/068277, dated Jul. 1, 2021, 7 pages.

International Preliminary Report on Patentability received for PCT Patent Application No. PCT/US2019/068280, dated Jul. 1, 2021, 7 pages.

International Preliminary Report on Patentability received for PCT Patent Application No. PCT/US2019/068282, dated Jul. 1, 2021, 9 pages.

International Search Report and Written Opinion received for PCT Patent Application No. PCT/US2019/065610, dated Mar. 26, 2020, 12 pages.

International Search Report and Written Opinion received for PCT Patent Application No. PCT/US2019/068275, dated Jun. 25, 2020, 16 pages.

Kapur NK et al. Mechanical circulatory support devices for acute right ventricular failure. Circulation. 2017; 136:314-326 (Year: 2017).

Sondergaard et al., "Transcatheter treatment of heart failure with preserved or mildly reduced ejection fraction using a novel interatrial implant to lower left atrial pressure", European Journal of Heart Failure, vol. 16, 2014, pp. 796-801.

International Search Report and Written Opinion received for PCT Patent Application No. PCT/US2019/042248, dated Oct. 23, 2019, 18 pages.

International Search Report and Written Opinion received for PCT Patent Application No. PCT/US2019/042252, dated Oct. 21, 2019, 18 pages.

International Search Report and Written Opinion received for PCT Patent Application No. PCT/US2021/013411, dated May 6, 2021, 11 pages.

Wei, X., Liu, X., Rosenzweig, A. What do we know about the cardiac benefits of exercise? Trends in Cardiovascular Medicine; 25(6) : 537-539. Aug. 2015 (Year: 2015).

International Search Report and Written Opinion received for PCT Patent Application No. PCT/US2019/068277, dated Mar. 25, 2020, 13 pages.

International Search Report and Written Opinion received for PCT Patent Application No. PCT/US2019/068280, dated Mar. 25, 2020, 12 pages.

International Search Report and Written Opinion received for PCT Patent Application No. PCT/US2019/068282, dated Mar. 25, 2020, 15 pages.

Tanaka Hikaru, et al., "Shinzo no Byouki to Chiryouaku", [online], Aug. 23, 2006, Internet URL: https://web.archive.org/web/20060823022639/https://www.mnc.tohou.ac.jp/v-lab/shinkin/medicine/medicine-1-2-1.html.

* cited by examiner

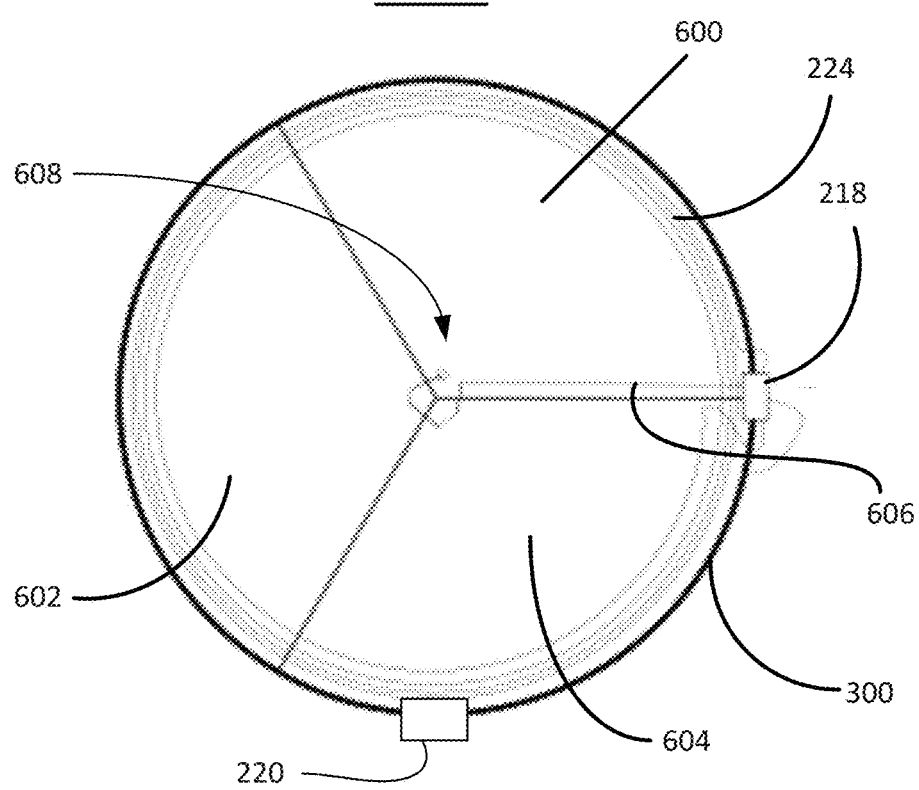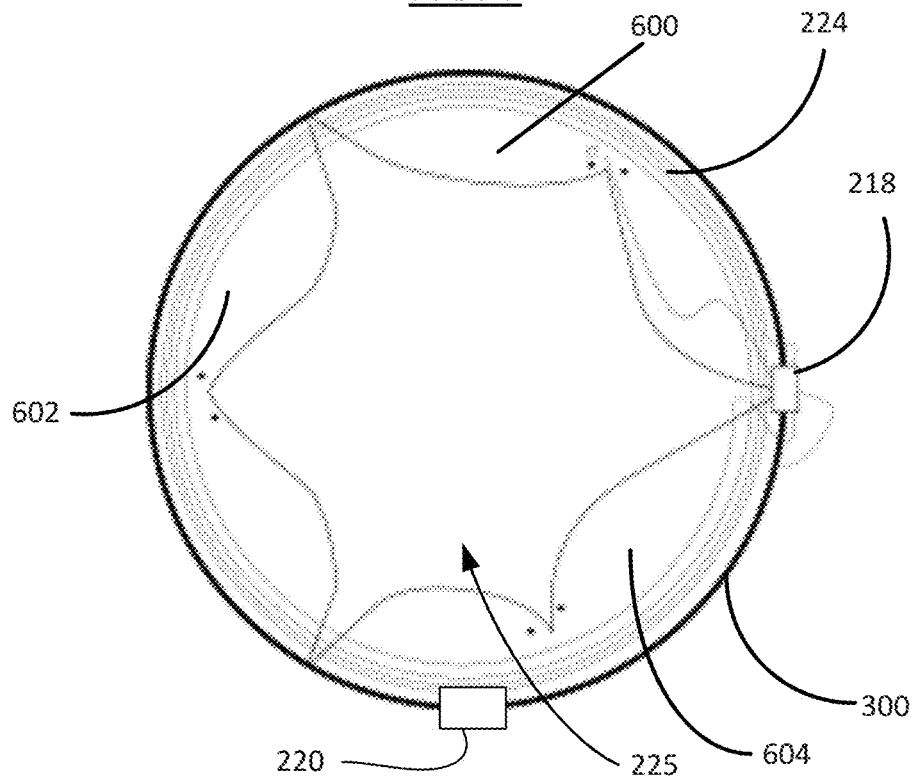

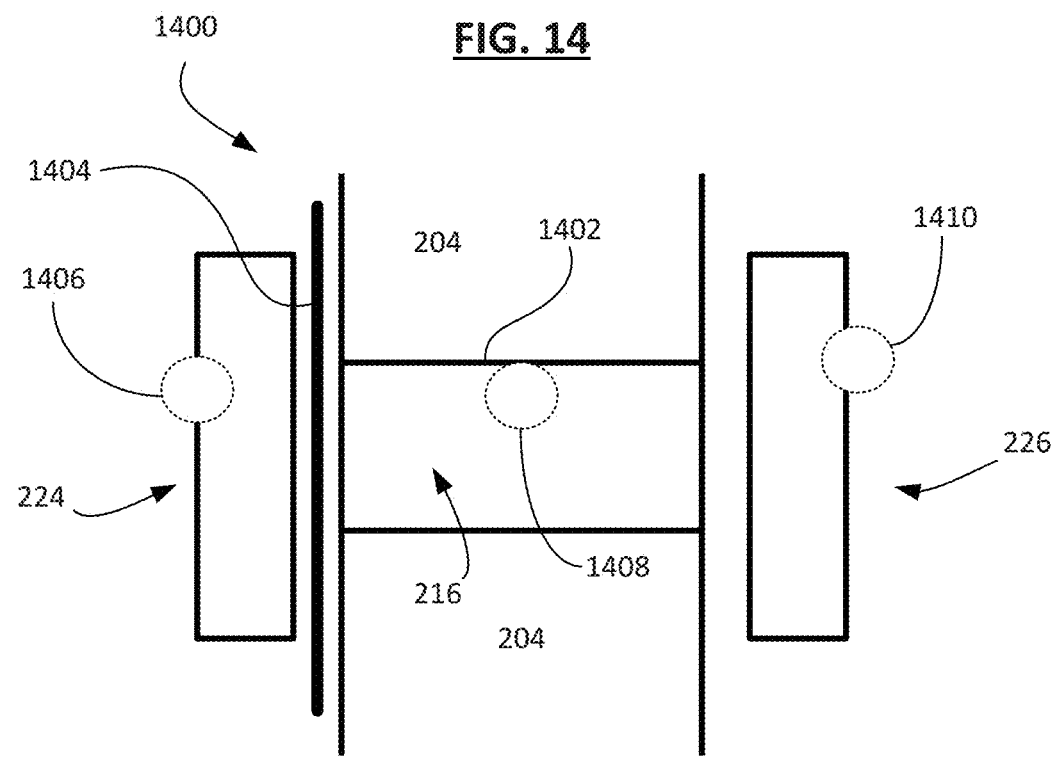
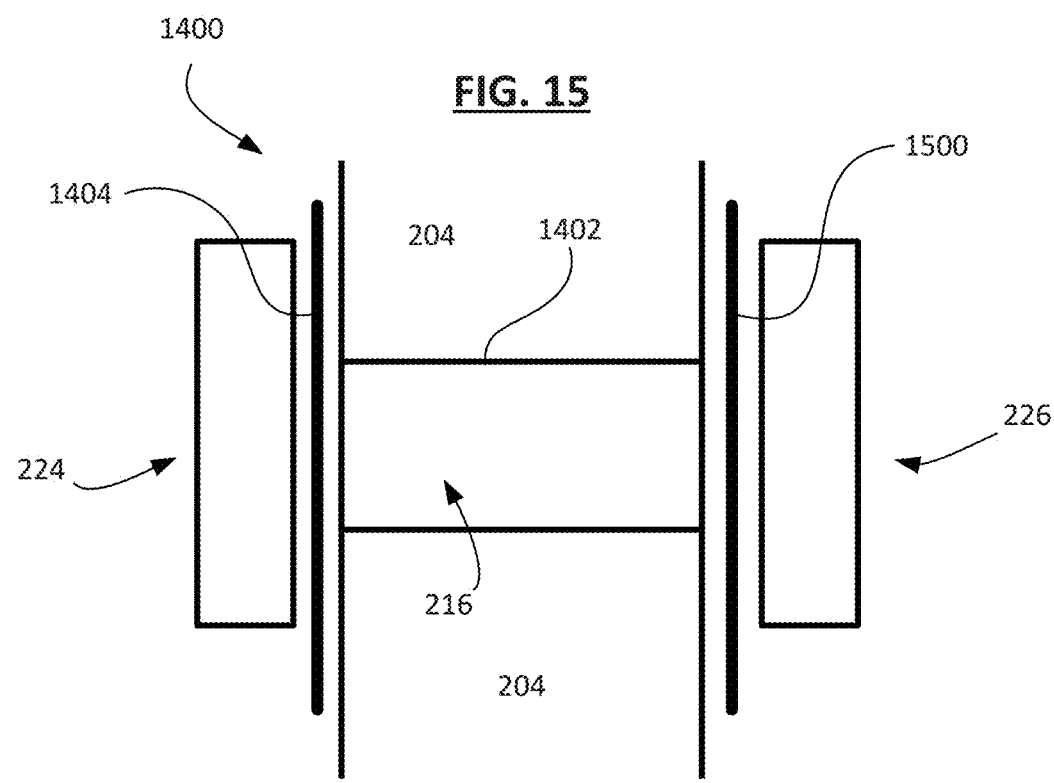

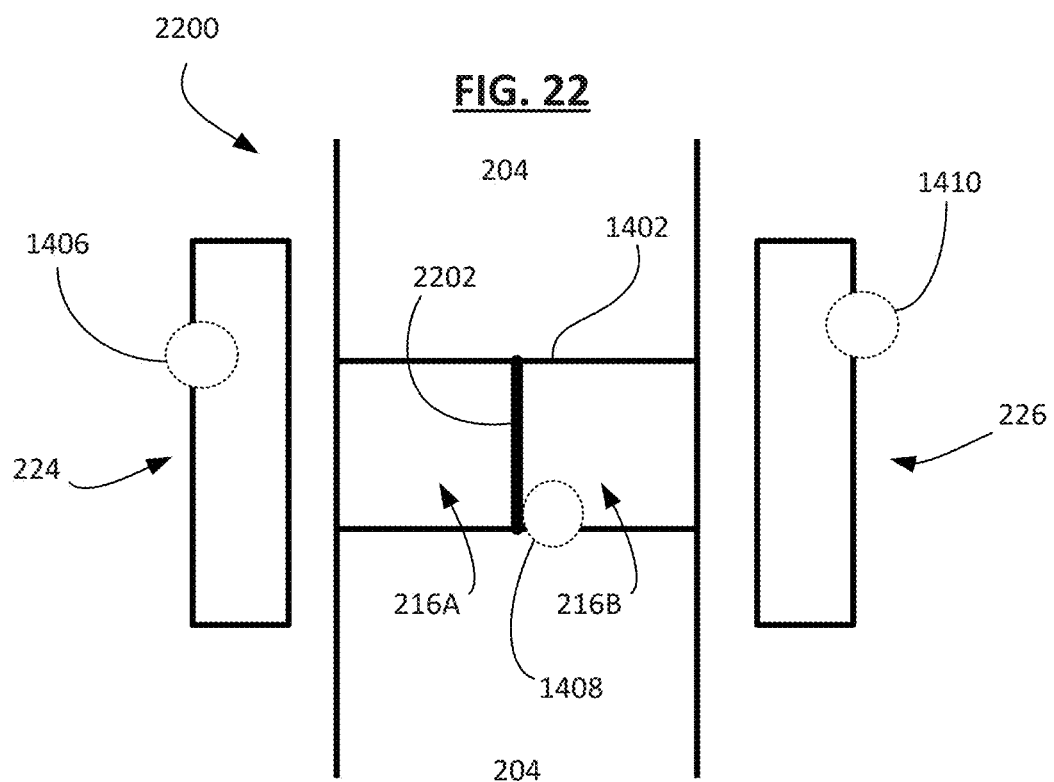

IMPLANTABLE MEDICAL DEVICE WITH ADJUSTABLE BLOOD FLOW

CROSS-REFERENCE TO RELATED APPLICATION

This application claims the benefit of Provisional Application No. 62/783,902, filed Dec. 21, 2018, Provisional Application No. 62/783,935, filed Dec. 21, 2018, Provisional Application No. 62/845,386, filed May 9, 2019, Provisional Application No. 62/894,260, filed Aug. 30, 2019, and Provisional Application No. 62/901,105, filed Sep. 16, 2019, all of which are incorporated herein by reference in their entireties for all purposes.

BACKGROUND

During the past decade, the number of coronary deaths in the United States has steadily decreased thanks to advancements in medical science and treatment, but the relative number of heart failure deaths has increased, indicating that more people are living with a high risk of heart failure than ever before. Generally, heart failure occurs when the heart cannot supply enough blood to the body. As a result, lower volume output leads to a higher filling pressure in the left heart to help compensate for the lack of output. Lower volume output also causes lower organ perfusion, including a reduction in kidney or renal perfusion. Reduced kidney perfusion can result in a retention of excess fluid. An acute decompensation episode is when fluid levels rise and/or vascular blood distribution declines to a state that causes the patient to experience fatigue and dyspnea (trouble breathing). If left untreated, this may result to serious complications and death.

It has been observed that heart failure primarily initiates as a result of left-side heart issues. In a normal healthy heart, oxygenated blood is first carried from the pulmonary veins, through the left atrium, into the left ventricle, and into the aorta, after which the blood is carried throughout the body. Thereafter, deoxygenated blood is carried from the two vena cavae into the right atrium, through the right ventricle, and into the pulmonary arteries, which then carry the blood into the lungs for oxygenation. The pumping performance of the left ventricle can be affected by the thickening/thinning of the left ventricular wall or by the aortic/mitral valve damage, causing less blood to be pumped to the rest of the body.

Advancements in effective treatment of heart failure in patients, including diagnosing and proactively avoiding the onset of heart failure, remain to be realized.

SUMMARY

According to one example, ("Example 1"), an implantable medical device includes: a fluid shunt adapted to extend through a wall separating a first cavity and a second cavity within the heart, the fluid shunt including a first portion adapted to extend into the first cavity within the heart, a second portion adapted to extend into the second cavity within the heart, and an intermediate portion interconnecting the first and second portions, the fluid shunt having a lumen extending between the first and second portions that is adapted to fluidly couple the first and second cavities within the heart; an occlusion assembly associated with the fluid shunt and adapted to selectively occlude flow through the lumen of the fluid shunt, the occlusion assembly being configured to be activated to adjust flow through the lumen of the fluid shunt; and at least one sensor assembly associated with the first portion of the fluid shunt such that the at least one sensor assembly is adapted to sense one or more physiologic parameters in the first cavity.

According to one example, ("Example 2"), further to Example 1, the at least one sensor assembly comprises a first sensor assembly and a second sensor assembly associated with the second portion of the fluid shunt such that the second sensor assembly is adapted to sense one or more physiologic parameters in the second cavity.

According to one example, ("Example 3"), further to Example 1, the implantable medical device includes a control unit in communication with the at least one sensor assembly. The control unit includes: a receiver coupled to the at least one sensor assembly, the receiver configured to receive physiologic parameter information from the at least one sensor assembly; and a processing unit coupled to the receiver for analyzing the physiologic parameter information received by the receiver.

According to one example, ("Example 4"), further to any preceding Example, the implantable medical device includes an actuation mechanism associated with the occlusion assembly, the control unit being operatively coupled to the actuation mechanism and configured to send a control signal to activate the actuation mechanism in response to the performed analysis.

According to one example, ("Example 5"), further to Example 4, the at least one sensor assembly is operably coupled to the actuation mechanism of the occlusion assembly such that upon the at least one sensor assembly sensing a predetermined physiologic measurement, the actuation mechanism is adapted to increase flow through the lumen of the fluid shunt.

According to one example, ("Example 6"), further to Example 1, at least one of the first and second portions of the fluid shunt includes a flange member for engaging the wall of the heart.

According to one example, ("Example 7"), further to Example 1, the fluid shunt includes a support.

According to one example, ("Example 8"), further to Example 7, the support includes a resilient framework.

According to one example, ("Example 9"), further to any preceding Example, the fluid shunt includes a cover that is impermeable to blood under physiologic conditions.

According to one example, ("Example 10"), further to Example 9, the cover includes a composite membrane material.

According to one example, ("Example 11"), further to any preceding Example, the first cavity is a left atrium of the heart and the second cavity is a right atrium of the heart.

According to one example, ("Example 12"), further to any preceding Example, the occlusion assembly is configured to be in a closed configuration such that the lumen of the fluid shunt is initially in a sealed state.

According to one example, ("Example 13"), further to any preceding Example, the occlusion assembly includes a thermal actuation mechanism configured to be activated by heating to adjust flow through the lumen of the fluid shunt.

According to one example, ("Example 14"), further to any one of Examples 9 to 12, wherein the cover is configured to be activated by being mechanically opened to adjust flow through the lumen of the fluid shunt.

According to one example, ("Example 15"), further to any one of Examples 9 to 12, the cover is configured to be activated by being thermally opened to adjust flow through the lumen of the fluid shunt.

According to one example, ("Example 16"), further to any one of Examples 9 to 12, the cover is configured to be selectively absorptive to ultrasound such that the membrane is configured to be thermally opened using an ultrasound source to adjust flow through the lumen of the fluid shunt.

According to one example, ("Example 17"), further to any one of Examples 9 to 12, wherein the cover is configured to be selectively absorptive to laser energy such that the membrane is configured to be thermally opened using a laser source.

According to one example, ("Example 18"), further to any one of Examples 9 to 12, the cover is configured to be selectively absorptive to radiofrequency energy such that the cover is configured to be thermally opened using a radiofrequency energy source.

According to one example, ("Example 19"), further to any one of Examples 9 to 12, the cover is configured to be selectively electrolytically degradable using an electrical energy source.

According to one example, ("Example 20"), further to Example 19, the occlusion assembly further includes at least one element operative to secure the cover in a closed configuration.

According to one example, ("Example 21"), further to Example 20, the at least one element operative to secure the cover in the closed configuration is configured to be selectively electrolytically degradable using an electrical energy source.

According to one example, ("Example 22"), further to Example 21, the electrical energy is supplied via magnetic induction.

According to one example, ("Example 23"), further to any one of Examples 13 to 22, wherein the occlusion assembly comprises a thermoplastic polymer membrane.

According to one example, ("Example 24"), further to any one of Examples 14 to 23, the cover is under radial tension to assist with opening of the membrane.

According to one example, ("Example 25"), further to any one of Examples 14 to 24, the cover exhibits residual stress profile to assist with opening of the membrane.

According to one example, ("Example 26"), further to any one of Examples 14 to 25, the cover is selectively openable between a plurality of opening sizes to modify flow through the lumen of the fluid shunt.

According to one example, ("Example 27"), further to any one of Examples 9 to 26, the cover is configured to cover the first portion of the fluid shunt that is adapted to extend into the first cavity within the heart.

According to one example, ("Example 28"), further to any one of Examples 9 to 27, the device includes a secondary cover, and the secondary cover is configured to cover the second portion of the fluid shunt that is adapted to extend into the second cavity within the heart.

According to one example, ("Example 29"), further to any one of Examples 1 to 8, the fluid shunt includes a membrane disposed in the lumen between the first and second portions that is impermeable to blood under physiologic conditions.

According to one example, ("Example 30"), further to any one of Examples 13 to 24, the device is part of a system including at least one of an extracorporeal induction energy source, an internal induction energy receiver, an ultrasonic energy source, a laser energy source, an RF energy source or another type of energy source for activating the occlusion assembly.

According to one example, ("Example 31"), further to any preceding Example, the device is configured to exhibit different resonant frequencies based upon a flow rate through the lumen of the fluid shunt.

According to one example, ("Example 32"), a method of treating a heart condition includes: sensing, by a first sensor assembly associated with a fluid shunt, one or more physiologic parameters in a first cavity within a heart, the fluid shunt being adapted to extend through a wall separating the first cavity within the heart and a second cavity within the heart; and adjusting flow through the fluid shunt by actuating an occlusion assembly associated with the fluid shunt.

According to one example, ("Example 33"), further to Example 32, the method includes sensing, by a second sensor assembly associated with the fluid shunt, one or more physiologic parameters in the second cavity within the heart.

According to one example, ("Example 34"), further to Example 32 or 33, the method includes: receiving, by a receiver coupled to at least the first sensor assembly, the physiologic parameters sensed by at least the first sensor assembly; performing, by a processing unit coupled to the receiver, analysis on the physiologic parameters received by the receiver to generate an actuation signal; and actuating the occlusion assembly according to the actuation signal.

According to one example, ("Example 35"), further to any one of Examples 32 to 34, the method includes sending, by a controller, the actuation signal to the occlusion assembly.

According to one example, ("Example 36"), further to any one of Examples 32 to 35, the controller is configured such that upon at least the first sensor assembly sensing a predetermined physiologic measurement, the controller sends the actuation signal to the occlusion assembly such that the occlusion assembly increases flow through the lumen of the fluid shunt.

According to one example, ("Example 37"), further to Example 32, the method includes: passing the fluid shunt through the wall of the heart; and including engaging flange portions of first and second portions of the fluid shunt with the wall of the heart.

According to one example, ("Example 38"), further to Example 32, the method includes: passing the fluid shunt through a wall of the heart separating the first cavity within the heart from the second cavity within the heart; and including engaging a support of the fluid shunt with the wall of the heart.

According to one example, ("Example 39"), further to Example 38, the support includes a resilient framework.

According to one example, ("Example 40"), further to any one of Examples 32 to 39, the fluid shunt includes a cover that is impermeable to blood under physiologic conditions.

According to one example, ("Example 41"), further to Example 40, the cover includes a composite membrane material.

According to one example, ("Example 42"), further to any one of Examples 32 to 41, the first cavity is a left atrium of the heart and the second cavity is a right atrium of the heart.

According to one example, ("Example 43"), a medical treatment system includes an implantable medical device and a deployment catheter. The implantable medical device includes: a fluid shunt adapted to extend through a wall separating a first cavity and a second cavity within the heart, the fluid shunt including a first portion adapted to extend into the first cavity within the heart, a second portion adapted to extend into the second cavity within the heart, and an intermediate portion interconnecting the first and second portions, the fluid shunt having a lumen extending between the first and second portions that is adapted to fluidly couple the first and second cavities within the heart; an occlusion assembly associated with the fluid shunt and adapted to selectively occlude flow through the lumen of the fluid shunt, the occlusion assembly being configured to be activated to adjust flow through the lumen of the fluid shunt; and at least one sensor assembly associated with the first portion of the fluid shunt such that the at least one sensor assembly is adapted to sense one or more physiologic parameters in the first cavity. The deployment catheter is configured to compress the implantable medical device and maintain the implantable medical device in a compressed configuration until the implantable medical device is deployed at a desired treatment location within the heart.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 6 shows an occlusion assembly of the implantable medical device according to an embodiment disclosed herein;

FIG. 7 shows the occlusion assembly of FIG. 6 with the membrane opened according to an embodiment disclosed herein;

FIG. 14 is a schematic diagram of an implantable medical device according to an embodiment disclosed herein;

FIG. 15 is a schematic diagram of an implantable medical device according to an embodiment disclosed herein;

FIG. 22 is a schematic diagram of an implantable medical device according to an embodiment disclosed herein.

Figure 1:
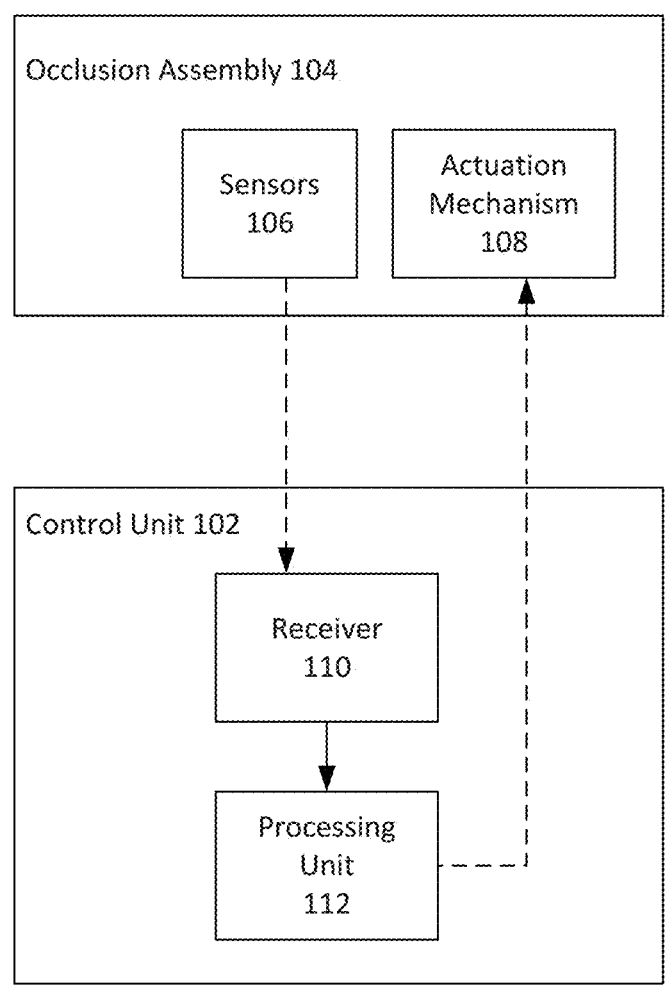
FIG. 1 is a schematic diagram of an implantable medical device according to an embodiment disclosed herein.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 20% of the stated value.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

Description of Various Embodiments

Various examples relate to noninvasive methods of monitoring cardiac pressure (e.g., left atrial pressure, or "LAP") in heart failure patients. Such monitoring may facilitate early warning of acute decompensation events, improved options for controlling cardiac pressure (e.g., LAP), among other potential advantages. Some examples relate to a heart failure management device that provides both titratable device-based therapy and hemodynamic monitoring. In some implementations, the heart failure management device includes a controllable cardiac shunt (e.g., intra-atrial shunt) and a sensor system for continuous noninvasive cardiac pressure measurement (e.g., LAP measurement), where flow through the shunt is controlled based upon cardiac pressure measurements from the sensor system. In some examples, the heart failure management device operates initially in a monitoring mode, and if symptoms worsen, controllable cardiac shunt is operable to modify cardiac pressure.

FIG. 1 shows an implantable medical device 100, according to some embodiments. As shown, the implantable medical device 100 has a control unit 102 and an occlusion assembly 104 controlled and maintained by the control unit 102. The occlusion assembly 104 is configured to be implanted in an organ wall (e.g., a septum of a heart) and includes one or more sensor assemblies 106 as well as an actuation mechanism 108. The control unit 102 includes a receiver 110 which receives from the sensor assemblies 106 physiologic parameter information data as measured by the sensor assemblies 106, and a processing unit 112 coupled to the receiver 110 which is optionally configured to analyze the physiologic parameter information received by the receiver 110.

The processing unit 112 can be a central processing unit (CPU), a system-on-a-chip (SoC), or any suitable processor. In some examples, the processing unit 112 completes analysis of the physiologic parameter information and determines to send a control signal to the actuation mechanism 108 associated with the occlusion assembly 104 to control the physiologic parameter within the heart.

The purpose of the actuation mechanism 108 is to open the occlusion assembly 104 to allow for a flow of fluid therethrough. In some embodiments, the actuation mechanism 108 is configured to activate when the sensor assemblies 106 detect certain conditions within the heart. In one example, the occlusion assembly 104 may be placed in a wall separating two chambers of the heart, such as the atrial wall. When the sensor assemblies 106 detect a differential between the blood pressure measurements within the left atria (also known as the "left atrial pressure" or LAP) and the right atria (also known as the "right atrial pressure" or RAP) beyond a threshold value, the actuation mechanism 108 may be activated in response to the elevated blood pressure differential to reduce the differential between the left and right atrium blood pressures. In some examples, the sensor assemblies 106 detect a single physiological measurement. In some examples, the sensor assemblies 106 detect a relative or absolute measurement.

In one example, the pressure measurements taken by the sensor assemblies 106 can be converted into a ratio of LAP to RAP. In general practice, an ideal ratio of LAP to RAP is 2:1 is desirable. Therefore, any ratio that is significantly smaller or larger than the desired ratio would pose a threat to the health of the heart, so the actuation mechanism 108 is activated to let some of the blood flow from one atrium to the other atrium, as appropriate, to bring the ratio closer to the desirable ratio. In another example, the threshold value may be determined by the physician who then decides under which conditions should the actuation mechanism 108 be activated. In another example, data from a single sensor assembly may be reported and this data used by a physician (or algorithm) to determine whether the actuation mechanism should be activated. It should be noted that other physiologic measurements may be used to make this decision, as explained below.

Figure 8:
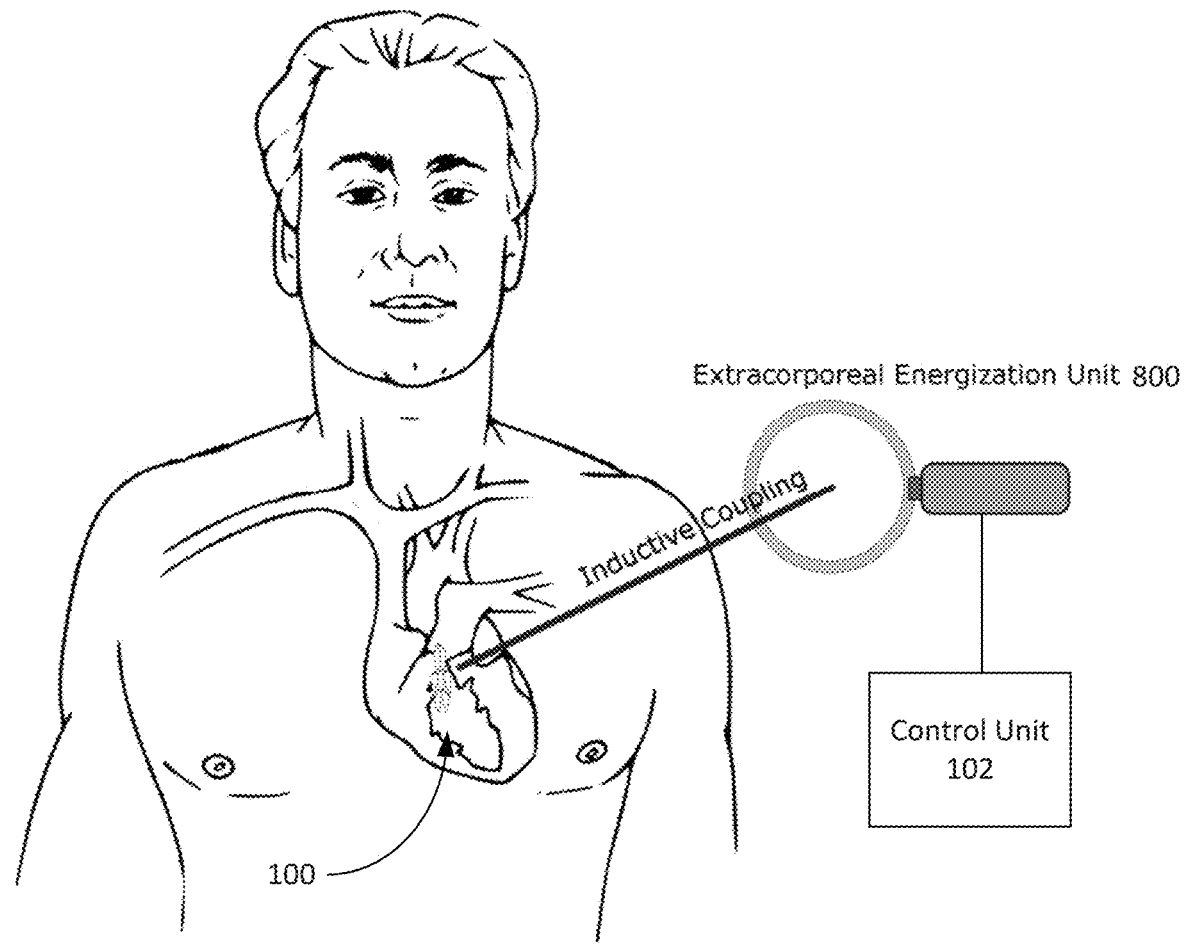
FIG. 8 shows an assembly to actuate the occlusion assembly according to an embodiment disclosed herein.

In some embodiments, the control unit 102 is configured to be located external to the body, as shown in FIG. 8 for example. For example, the receiver 110 is optionally configured to receive the information wirelessly and the processing unit 112 is optionally configured to send the control signal wirelessly. The actuation mechanism 108 may be activated in response to receiving the control signal, such as an activation signal transmitted by the processing unit 112. In this example, the actuation mechanism 108 may also be coupled to a receiver capable of receiving such signal from an external source.

Figure 2:
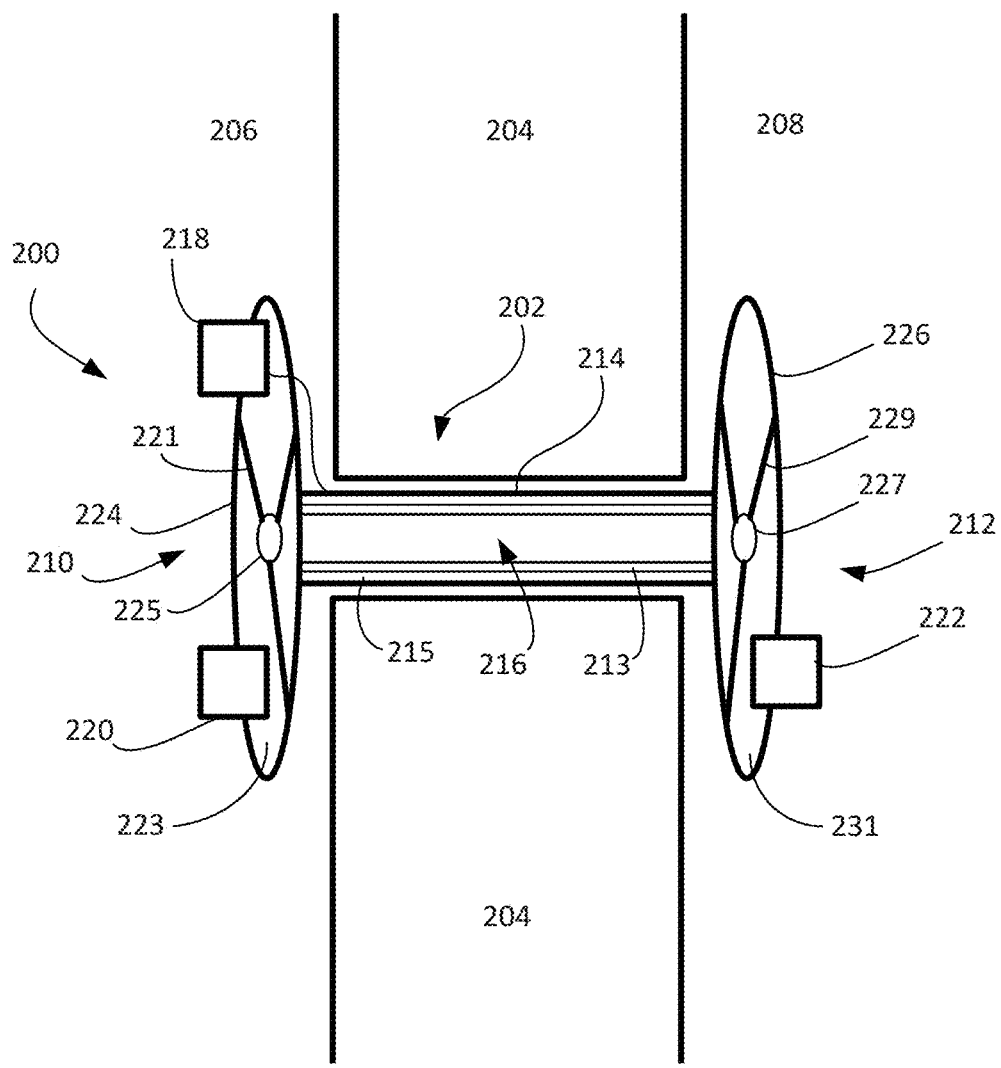
FIG. 2 shows an occlusion assembly of the implantable medical device according to an embodiment disclosed herein.

FIG. 2 shows an implantable medical device 200, according to some embodiments. The implantable medical device 200 includes a fluid shunt 202 adapted to extend through an organ wall 204 (e.g., a septum) separating a first cavity 206 (e.g., a first heart chamber) and a second cavity 208 (e.g., a second heart chamber) within a body of a patient. In some examples, the cavities are the left and right atria or the left and right ventricles, for example. In another example, one or more of the cavities are an aorta, a vena cava, or other vascular structure.

In some examples, the fluid shunt 202 includes a first portion 210 adapted to extend into the first cavity 206, a second portion 212 adapted to extend into the second cavity 208, and an intermediate portion 214 interconnecting the first portion 210 and the second portion 212. The fluid shunt 202 also has a lumen 216 extending through the intermediate potion 214 between first portion 210 and the second portion 212. The lumen 216 is adapted to provide a fluid path between, or to fluidly couple, the first cavity 206 with the second cavity 208.

In some embodiments, the first portion 210 includes a first flange 224. The first flange 224 may be annular in shape, having a first aperture 225 and including a first flange support 221 and a first flange cover 223. The first flange support 221 can be a resilient framework including one or more frame elements, which may be wound, woven, braided, cut, or otherwise formed. In various examples, the first flange support 221 is formed of a shape memory material, such as a shape memory alloy (e.g., a nickel-titanium alloy). The first flange cover 223 optionally includes a membrane material (e.g., an ePTFE membrane) or other biocompatible material as desired. In some examples, the first flange cover 223 is configured to promote or inhibit tissue ingrowth and/or is biodegradable under physiologic conditions over time.

Figure 3:
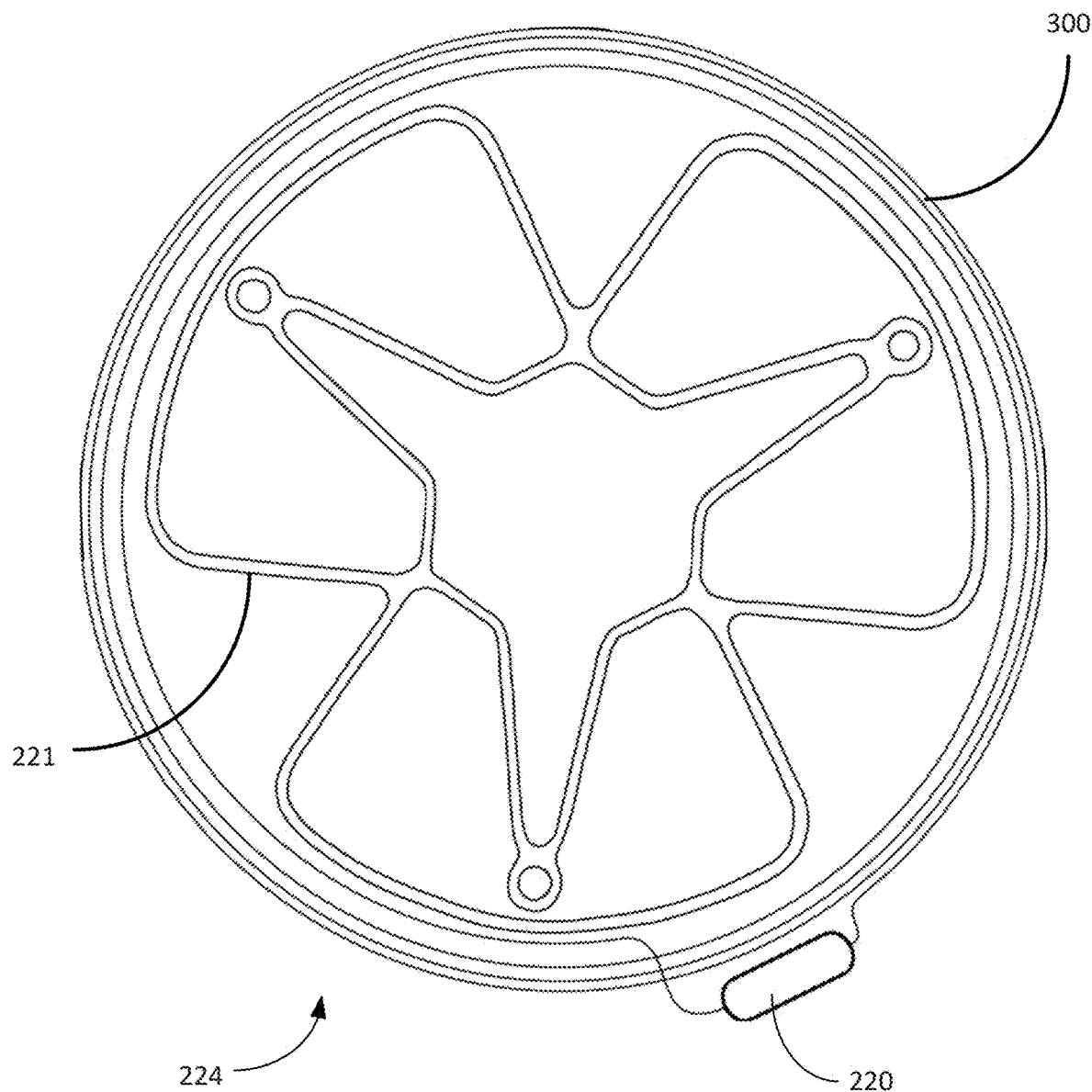
FIG. 3 shows an occlusion assembly of the implantable medical device according to an embodiment disclosed herein.
Figure 4:
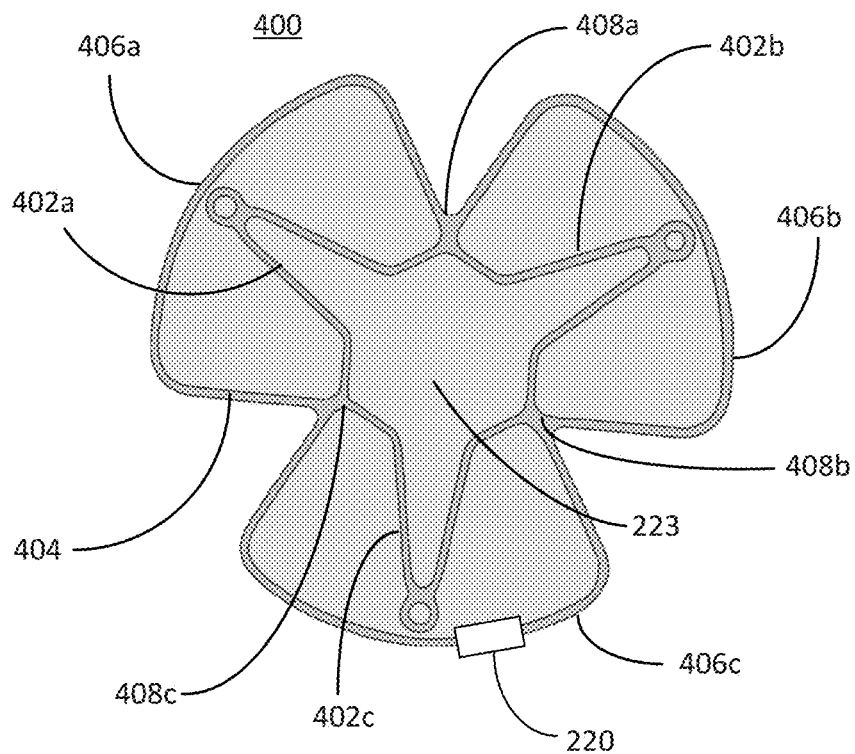
FIG. 4 shows an occlusion assembly of the implantable medical device with a membrane according to an embodiment disclosed herein.
Figure 5:
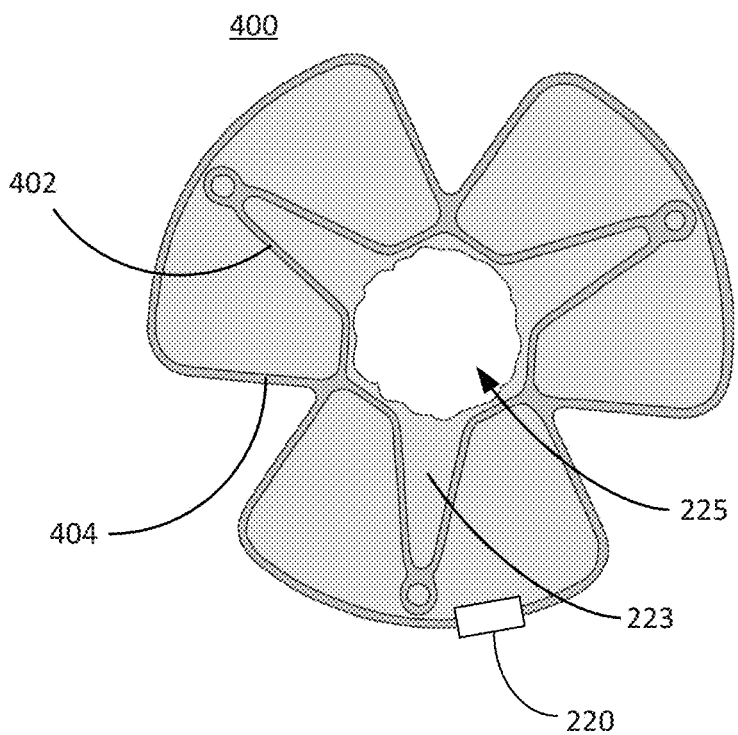
FIG. 5 shows the occlusion assembly of FIG. 4 with the membrane opened according to an embodiment disclosed herein.

FIGS. 3-5 show different embodiments and examples of the flanges as previously introduced. FIG. 3 shows the first flange 224 according to an embodiment where the first flange 224 engages with the organ wall 204 and is attached to an antenna 300. A sensor assembly 220 attaches to the antenna 300, and the antenna 300 is operative to send the physiologic measurement information provided by the sensor assembly 220. In some embodiments, an occlusion assembly 218, as explained below, is also attached to the antenna 300. The antenna 300 is operative to receive the control signal sent to the occlusion assembly 218, or more specifically to the actuation mechanism 108 of the occlusion assembly 218. In one example, the implantable medical device 200 has a second flange 226 at the second portion 212 with a second flange cover 231 to prevent fluid flow between the lumen 216 and a second cavity 208. In some embodiments, the first flange cover 223 and/or the second flange cover 231 include a composite membrane material, such as a polymer membrane. In one example, the polymer membrane is expanded polytetrafluoroethylene (ePTFE). In another example, the membrane can be any other suitable fluoropolymer, thermoplastic polymer, elastomer, biopolymer, fabric, textile, etc. In some examples, the second flange 226 has a configuration that is similar, if not identical, to that of the first flange 224.

FIGS. 4 and 5 show a first frame portion 400 according to an embodiment. In some examples, the first frame portion 400 forms part of the first flange 224 of the implantable medical device 200. The first frame portion 400 may be covered by, or otherwise support flange cover 223 which may be configured to be impermeable to bodily fluids such as blood under physiologic conditions to act as a separator to help prevent fluid flow between the lumen 216 and the first cavity 206. As shown, the first frame portion 400 can include one or more outer lobes (e.g., a first outer lobe 406a, a second outer lobe 406b, and a third outer lobe 406c) and an inner frame portion 402 (which in this example defines three inner lobes 402a, 402b, and 402c). Each of the lobes 406a, 406b, and 406c may be attached to the inner frame portion 402 such that the lobes are equally spaced around the inner frame portion 402. In some instances, the lobes may be attached to the inner frame portion 402 and/or to adjacent lobes at attachment points 408a, 408b, and 408c. For example, in some instances, the first lobe 406a is attached to the second lobe 406b at attachment point 408a, the second lobe 406b is attached to the third lobe 406c at attachment point 408b, and the third lobe 406c is attached to the first lobe 406a at attachment point 408c. Although FIGS. 4 and 5 are described with reference to three lobes and three attachment points, the first frame portion 400 can have any number of lobes and respective attachment points as desired.

When present, the inner frame portion 402 can be any shape as desired. For example, in some instances, the inner frame portion 402 is substantially circular or substantially triangular (as shown in FIGS. 4 and 5). In some instances, the inner lobes 402a, 402b, and 402c may extend into the first, second and third lobes 406a, 406b, 406c to define the shape of the inner frame portion 402. In some examples, the first frame portion 400 includes the sensor assembly 220 attached thereto. In some examples, the sensor assembly 220 is operatively coupled to the antenna 300 as shown in FIG. 3.

Though not shown in FIGS. 4 and 5, and similarly to the first flange 224, the second flange 226 of the implantable medical device 200 can include a second frame portion that has the same or a different number of lobes as the first frame portion 400. For example, in some instances, the first and second frame portions each have three lobes. In other instances, the first frame portion 400 may include three lobes while the second frame portion includes two, four, five, or more lobes. In some instances, the first frame portion 400 can have lobes that are larger, smaller, and/or a different shape than the lobes of the second frame portion. Furthermore, in some examples, the first frame portion 400 can include one or more sensor assemblies (e.g., 220 and 222) and the antenna 300, as shown in FIG. 3.

Furthermore, though not shown in FIGS. 4 and 5, in certain instances, the implantable medical device 200 may include a pattern of structural frame elements or other structural features that form the first flange 224 and/or the second flange 226. The pattern of structural frame elements may be arranged (e.g., project from) inside inner lobes 402a, 402b, and 402c, and may be included in any of the lobes of devices discussed herein. If desired, the pattern of structural frame elements can be arranged to form an open cell pattern. For example, the pattern of structural frame elements can form a diamond cell pattern in the inner lobes 402a, 402b, and 402c that collapse and open during load and deployment of the implantable medical device 200 in a catheter. The pattern of structural frame elements may enhance radial strength during deployment and facilitate arrangement of the implantable medical device 200 in a deployed, or otherwise operative shape.

FIG. 5 shows the first flange cover 223 after the actuation mechanism 108 creates a first aperture 225 in the cover 223 to allow for fluid flow through the lumen 216. In some embodiments, the first aperture 225 is formed through mechanical or interventional procedures. In some embodiments, the first aperture 225 is formed through non-invasive procedures.

Referring back to FIG. 2, in some embodiments, the second portion 212 includes the second flange 226. The second flange 226 may be annular in shape, having a second aperture 227 and including a second flange support 229 and a second flange cover 231. The second flange support 229 can also be a resilient framework including one or more frame elements, which may be wound, woven, braided, cut, or otherwise formed. In various examples, the second flange support 229 is formed of a shape memory material, such as a shape memory alloy (e.g., a nickel-titanium alloy). The second flange cover 231 optionally includes a membrane material (e.g., an ePTFE membrane) or other biocompatible material as desired. In some examples, the second flange cover 226 is configured to promote or inhibit tissue ingrowth and/or is biodegradable under physiologic conditions over time.

In some embodiments, the intermediate portion 214 of the fluid shunt 202 includes a tubular member 215 and an intermediate support 213 configured to help maintain the shape of the tubular member 215 against compression and/or distortion forces exerted by the patient anatomy (e.g., the wall 204) and/or physiologic processes (e.g., blood pressure). The intermediate support 213 can also be a resilient framework including one or more frame elements, which may be wound, woven, braided, cut, or otherwise formed. In various examples, the intermediate support 213 is formed of a shape memory material, such as a shape memory alloy (e.g., a nickel-titanium alloy). The tubular member 215 optionally includes a membrane material (e.g., an ePTFE membrane) or other biocompatible material as desired. In some examples, the tubular member 215 is configured to promote or inhibit tissue ingrowth and/or is biodegradable under physiologic conditions over time.

As indicated generally in FIG. 2, the implantable medical device 200 also includes the occlusion assembly 218, as mentioned above, associated with the fluid shunt 202. In some examples, the occlusion assembly 218 is adapted to selectively occlude flow through the lumen 216 of the fluid shunt 202. For example, the occlusion assembly 218 can be configured to be activated (via physical, manual intervention or via remote or automatic means) to adjust flow through the lumen 216 of the fluid shunt 202.

In some examples, the actuation mechanism 108 is configured to be actuated to permit fluid flow through the lumen 216, or to permit increased or decreased fluid flow through the lumen 216. In some examples, the actuation mechanism 108 is selectively activated to increase and decrease flow, for example by being actuatable to open or narrow the lumen 216. The actuation mechanism 108 is optionally positioned at the first portion 210, the second portion 212, and/or the intermediate portion 214. The actuation mechanism 108 may be "one-way" actuatable, in that the actuation mechanism 108 begins at a no-flow, or low-flow condition, and then can be opened (e.g., entirely or in stages), to increase flow. In other embodiments, the actuation mechanism 108 can both increase and decrease flow through the fluid shunt 202.

In one example, the actuation mechanism 108 includes a needle or other suitable puncturing component to mechanically penetrate one or both of the flange covers 223 and 231. In one example of an interventional procedure, a needle is led to the location of the implantable medical device 200 by a catheter, and the needle is used to form the first aperture 225 by puncturing the first flange cover 223 and the second aperture 227 by puncturing the second flange cover 231. Other interventional procedures include mechanical, thermal, laser, ultrasound, and inductive methods.

In one example shown in FIG. 6, the actuation mechanism 218 is attached to the antenna 300. The membrane defining the first flange cover 223 is made of three flap elements 600, 602, and 604 that are under radial tension, with a wire 606 fixing the three flap elements together with a stitch 608 as shown to prevent the radial tension from causing the flap elements to move toward the outer edge of the first flange 224. The sensor assembly 220 is located on the antenna 300. Upon receiving the actuation signal from the control unit 102, the actuation mechanism 218 pulls the wire 606 to cause the flap elements 600, 602, and 604 to be pulled back toward the outer edge, thereby creating the first aperture 225 as shown in FIG. 7. The wire 606 can be made of any suitable material. In some examples, the wire 606 is a thread made of polymers such as nylon or PTFE. In some examples, the wire 606 is made of a conductive material, such as stainless steel or nickel-titanium alloy, among others. In one example, the same actuation mechanism may also be attached to the second flange cover 231, with the second flange cover 231 also made of similar flap elements. In one example, the number of flap elements may be two. In other examples, the number of flap elements may be four or more.

Various additional or alternative actuation mechanisms are contemplated. In some examples, the wire 606 is conductive, and upon receiving the actuation signal from the control unit 102, the occlusion assembly 218 applies a voltage to the wire 606 to cause the wire 606 to undergo electrolytic degradation. After undergoing sufficient degradation, the wire 606 breaks or dissolves and can no longer hold the flap elements 600, 602, and 604 together. As such, the flap elements 600, 602, and 604 retract or open from the initial position shown in FIG. 6, thereby creating the first aperture 225 as shown in FIG. 7.

In some examples, the actuation mechanism 108 is external to the body, such as an extracorporeal energization unit 800. FIG. 8 illustrates the implantable medical device 100 or 200. Energy is inductively supplied to the implantable medical device using the extracorporeal energization unit 800 in a treatment system according to an embodiment. The energization unit 800 can include an extracorporeal induction energy source which supplies power to the implanted medical device so that electrical energy can electrolytically degrade an element 606 thereby forming the first aperture 225, converting the device to an open configuration. In some examples, the control unit 102 is configured to be located external to the body and controls the extracorporeal energization unit 800. In some embodiments, the treatment system which operates to control the first aperture 225 in the implantable medical device 200 includes one or more of: an internal induction energy receiver, an ultrasonic energy source, a laser energy source, a radiofrequency (RF) energy source, and/or another type of energy source for activating the occlusion assembly 104. Furthermore, in some embodiments, when the first aperture 225 is formed and fluid flow is allowed within the lumen 216, the implantable medical device 200 exhibits different resonant frequencies based upon a flow rate through the lumen 216. The resonant frequency can be measured using one or both of the sensor assemblies 220 and 222 coupled to the implantable medical device 200. In one example, the resonant frequency measured by the receiver 110 is converted to a physiologic parameter such as the fluid flow rate by the processing unit 112. In one example, both of the sensor assemblies 220 and 222 are pressure sensors, so the flow rate of fluid through the lumen 216 is estimated based upon the lumen's dimensions, the pressure differential, and the known fluid dynamic characteristics of the fluid, which may be blood. Additional or alternative sensing features are contemplated. In some examples, a shift in resonant frequency measured by the sensor assembly 220 or 222 provides verification that the lumen 216 is successfully opened to allow fluid flow therethrough.

In some embodiments, the wireless extracorporeal energization includes inductive energy transfer or ultrasound energy transfer, which are non-limiting examples of the noninvasive procedures. In one embodiment, a membrane of the flange cover 223 can be melted to form the aperture 225 after exposing the flange cover 223 to thermal or ultrasound energy, to produce a thermal activation mechanism. In some examples, the size of the aperture 225 can be adjusted by varying the amount of thermal activation. For reference, if desired, the aperture 227 in the flange cover 231 may be formed using the same method/mechanism as any of those described in association with the flange cover 223, or by differing methods as desired.

In another embodiment, the flange cover 223 is made of at least one flap element which is controlled mechanically by the actuation mechanism 108, which is in turn controlled wirelessly by the control unit 102. In one example, mechanism control is accomplished by the actuation mechanism 108 pulling on the flap element to change the state of the flap element from a closed state to a more open state. The size of the aperture 225 can be adjusted by varying how much the flap element is to be displaced from the closed position. In some embodiments, the actuation mechanism 108 can also control the flap element to decrease the size of the aperture 225 by returning the position of the flap element closer to the closed position. In one example, the controlling of the at least one flap element is done by the actuation mechanism 108 of the occlusion assembly 218 applying a voltage to induce electrolytic degradation of the wire (for example, the wire 606 shown in FIG. 6) which holds the at least one flap element in the closed state, thereby causing the at least one flap element to change from the closed state to a more open state.

In some embodiments that are configured to utilize noninvasive procedures for actuation, one or both of the covers 223 and 231 are made of a membrane that is selectively absorptive to ultrasound such that the membrane is configured to be thermally opened using an ultrasound source to adjust flow through the lumen 216 of the fluid shunt 214. In some embodiments configured to utilizing noninvasive actuation procedures, one or both of the covers 223 and 231 are made of a membrane that is selectively absorptive to RF energy such that the membrane is thermally opened using an RF ablation source to adjust flow through the lumen 216 of the fluid shunt 214. In some embodiments, the membrane is selectively absorptive to laser energy such that the membrane is configured to be thermally opened using a laser source. In some embodiments, the membrane or the elements (e.g., wires) holding the membrane in place are selectively and electrolytically degradable using electrical energy supplied by an induction energy source. In some examples, the electrical energy can be supplied by any suitable means such as a battery, a piezoelectric receiver exposed to an ultrasonic energy source, magnetic induction, a radiofrequency (RF) energy source, and/or another type of energy source for activating the occlusion assembly. In some embodiments, both covers 223 and 231 are actuatable utilizing similar methods. For example, the covers 223 and 231 can both be configured to open simultaneously in response to receiving energy from an external source, e.g. RF energy, laser energy, induction energy, or others.

In some embodiments, one or both of the covers 223 and 231 are under radial tension to assist with forming one or both of the apertures 225 and 227. For example, when the cover(s) 223 and 231 are stretched, even a small opening in the covers can be enlarged when the radial tension placed from the outer edge of the covers pull the cover material surrounding the opening away from the locations of the openings in a plurality of directions. In some embodiments, the cover(s) exhibit residual stress profile to assist with forming the one or both of the apertures 225 and 227 in the cover. In some embodiments, the cover(s) are selectively openable between a plurality of sizes for the one or both of the apertures 225 and 227 to modify flow through the lumen 216.

Figure 9:
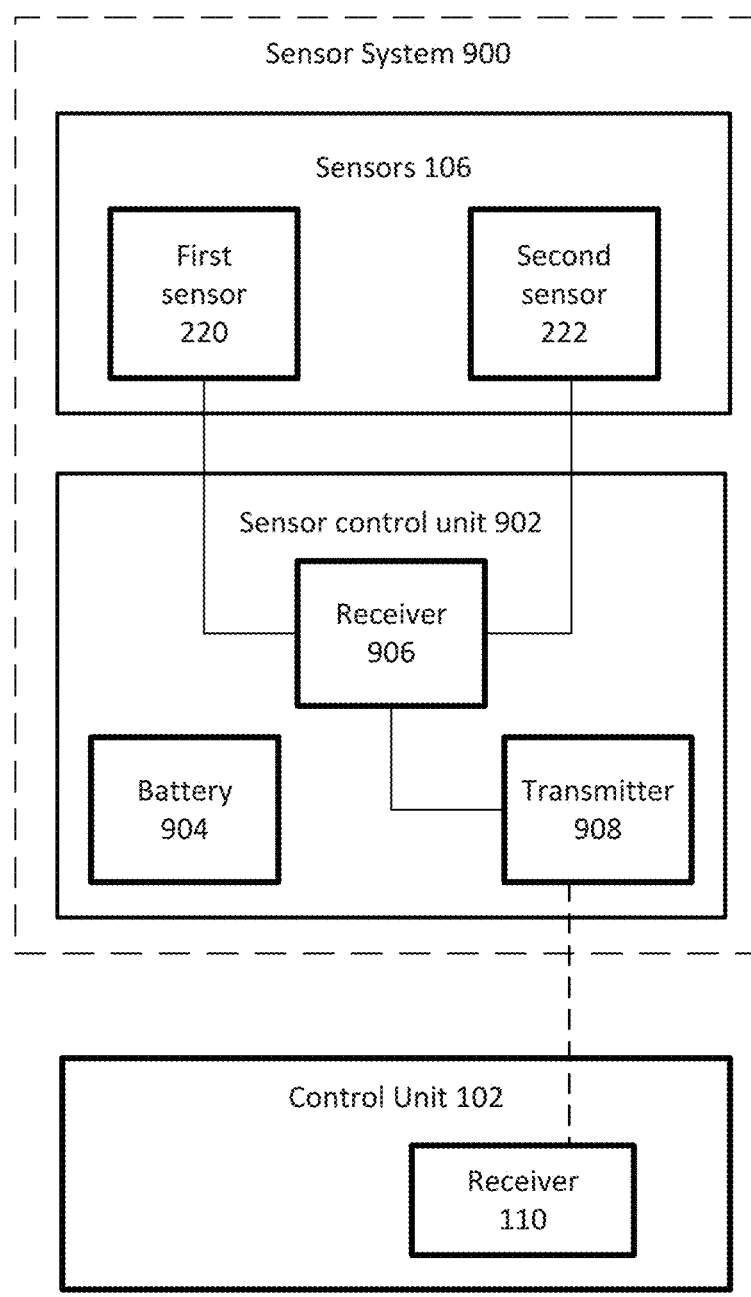
FIG. 9 shows a sensor system implemented in the implantable medical device according to an embodiment disclosed herein.

FIG. 9 shows a sensor system 900 implemented in one embodiment of the implantable medical device 100. In some examples, the sensor system 900 includes one or more sensor assemblies 106 and a sensor control unit 902 in communication with the one or more sensor assemblies 106. In one example, the one or more sensor assemblies 106 are active sensors that include transmitters that send out a signal and records the environmental response to the signal. In another example, the one or more sensor assemblies 106 are passive sensors that require external energy sources to perform physiological measurements, for example upon receipt of an input from the physical environment. The sensor control unit 902 includes a battery 904, a receiver 906, and a transmitter 908. The battery 904 provides power for the sensor assemblies 106 to continue taking physiological measurements as well as for the sensor control unit 902 to receive and transmit data of said measurements. The receiver 906 receives the measurement data from the sensor assemblies 106, and the transmitter 908 transmits the data, for example wirelessly, to the external control unit 102.

In some examples, the one or more sensor assemblies 106 include a first sensor assembly 220 associated with the first portion 210 of the fluid shunt 202 adapted to sense one or more physiologic parameters in the first cavity 206 and a second sensor 222 associated with the second portion 212 of the fluid shunt 214 adapted to sense one or more physiologic parameters in the second cavity 208 within the heart. Although two sensor assemblies are shown and described, greater (e.g., three or more) or fewer (e.g., a single sensor) are contemplated. In one example, one or all of the sensor assemblies 106 are configured to sense a physiologic parameter including blood pressure levels in the respective cavities. In some examples, one or more sensor assemblies 106 are configured to sense the rate at which blood flows in the designated cavity within the heart. In still further examples, one or more sensors are configured to sense temperature of the blood. In still other examples, one or more sensors are configured to sense oxygen saturation of the blood.

Examples of suitable sensors capable of measuring fluid flow or pressure inside an organ include piezoelectric sensors, pressure switches, optical pressure transducers, Venturi meters, impedance monitors, and ultrasonic pressure sensors, as well as other types of electrophysiologic and hemodynamic sensors.

Figure 10:
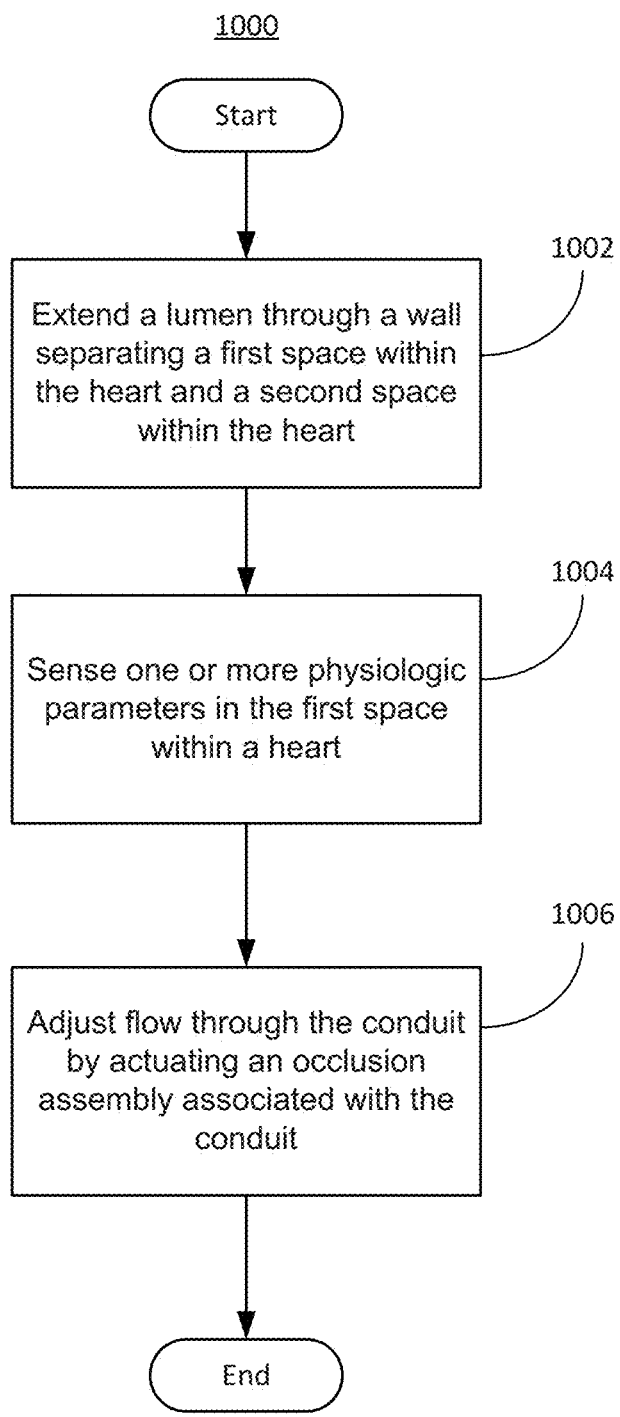
FIG. 10 shows a method of operating the implantable medical device according an embodiment disclosed herein.

FIG. 10 shows a method 1000 of operating the implantable medical device 200 according to one embodiment. In the first step 1002, the lumen 216 is extended through the wall 204 separating the first cavity 206 within the heart and the second cavity 208 within the heart. In one example, the fluid shunt 214 is passed through the wall 204 of the heart, including engaging flange portions, or anchors 224 and 226, of the first portion 210 and the second portion 212 of the fluid shunt 214 with the wall 204 of the heart. In step 1004, the first sensor assembly 220 senses one or more physiologic parameters in the first cavity 206. In the following step 1006, the flow through the fluid shunt 214 is adjusted by actuating the occlusion assembly 218 associated with the fluid shunt 214.

Figure 11:
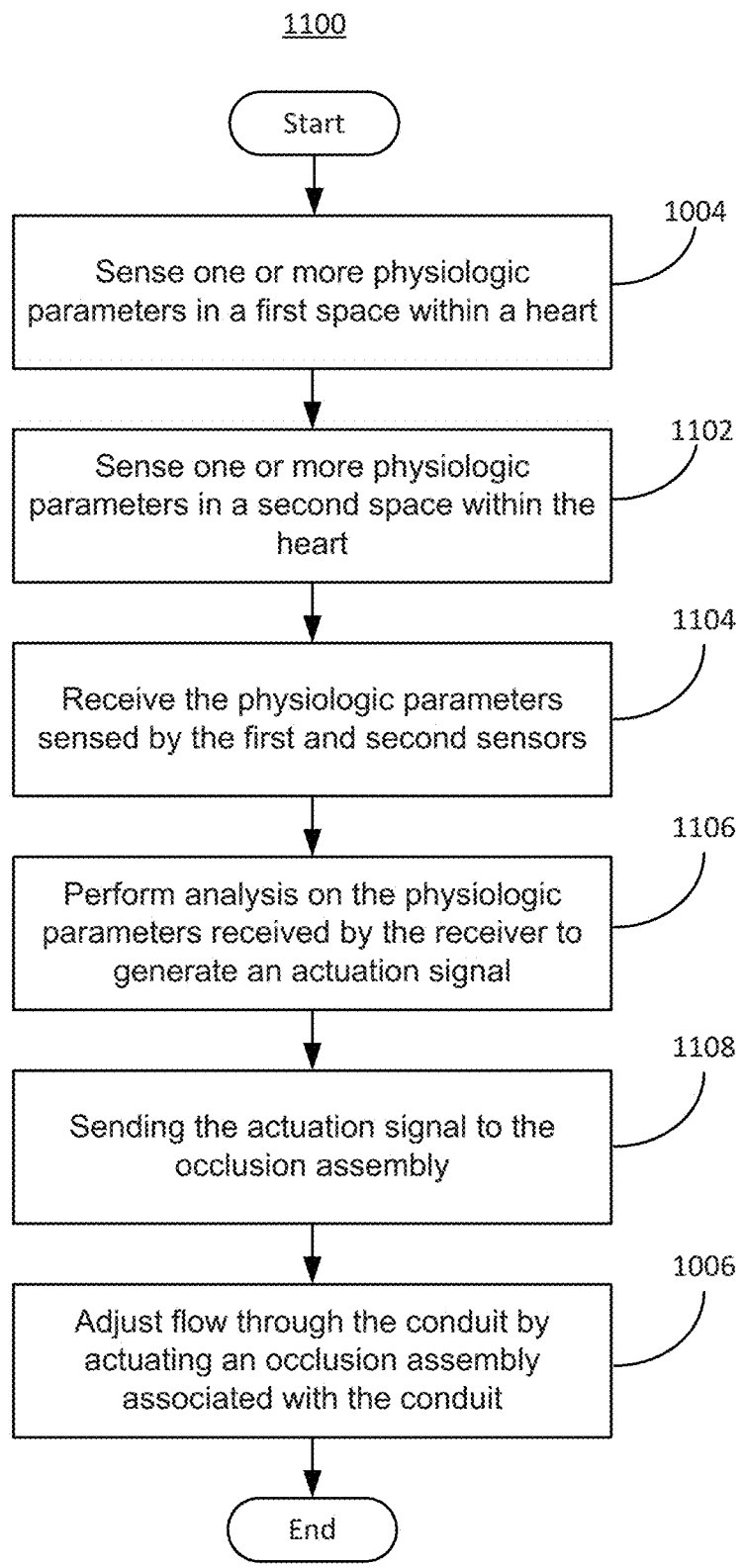
FIG. 11 shows a method of operating the implantable medical device according to an embodiment disclosed herein

FIG. 11 shows another method 1100 of operating the implantable medical device 200 according to some embodiments. In step 1102 following the aforementioned step 1004, the second sensor 222 senses one or more physiologic parameters in the second cavity 208 within the heart. In step 1104, the receiver 110 receives the physiologic parameters sensed by the first sensor assembly 220 and the second sensor 222. In the next step 1106, the processing unit 112 performs analysis on the physiologic parameters received by the receiver 110 to generate an actuation signal. In step 1108, the control unit 102 sends the actuation signal to the occlusion assembly 218. Finally, in step 1006, the flow through the fluid shunt 214 is adjusted by actuating the occlusion assembly 218 associated with the fluid shunt 214 according to the actuation signal provided by the processing unit 112 of the control unit 102.

In some embodiments, the control unit 102 sends the actuation signal to the occlusion assembly 218 upon the first sensor assembly 220 and the second sensor 222 sensing a predetermined differential physiologic measurement such that the occlusion assembly 218 increases flow through the lumen 216 by performing one or more of the procedures as explained above.

Figure 12:
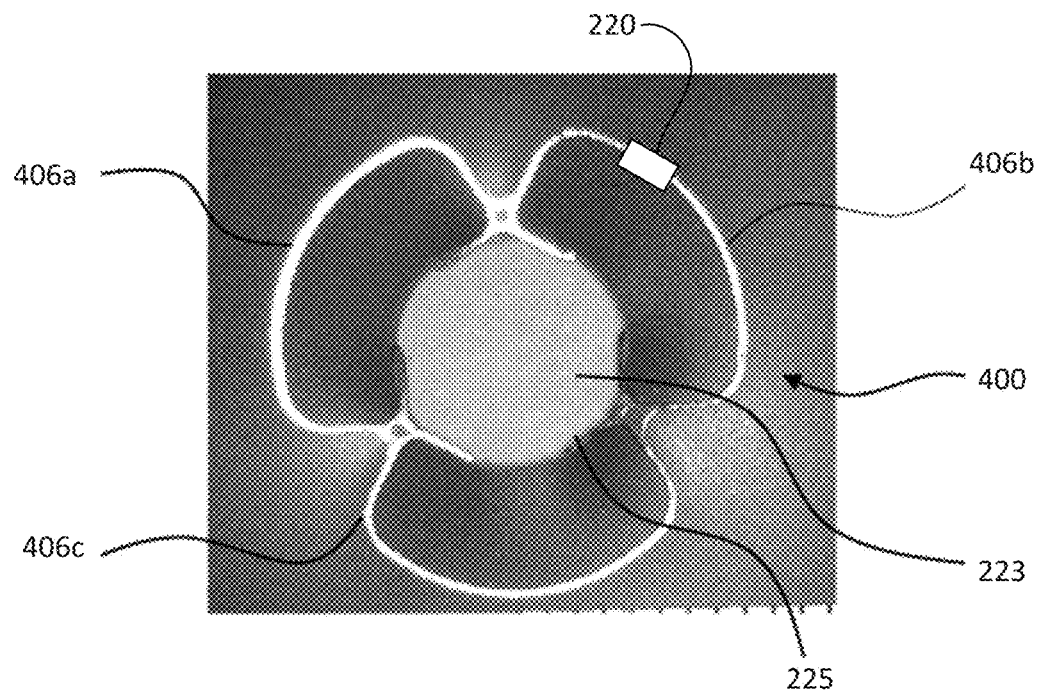
FIG. 12 shows an implantable medical device according to an embodiment disclosed herein as viewed from one side of the device.

FIG. 12 is an image of a first side of the implantable medical device 200, where the first frame portion 400 of the first flange 224 as shown in FIGS. 4 and 5 is visible, including a covering material for the flange cover 223, in accordance with an embodiment. As shown, in some instances, the covering material 223 can be arranged over the opening or aperture 225. Thus, the covering material 223 may act to slow or occlude flow through the first frame portion 400 as desired. In some instances, the covering material 223 can be arranged over the first frame portion 400. In some instances, the covering material 223 may be attached to one or more of the first lobe 406a, the second lobe 406b, and the third lobe 406c. In some instances, the inner frame portion 402 serves as the second frame portion 1300, as shown and discussed with reference to FIG. 13. In some examples, the sensor assembly 220 is located on one or more of the first lobe 406a, the second lobe 406b, and the third lobe 406c.

Figure 13:
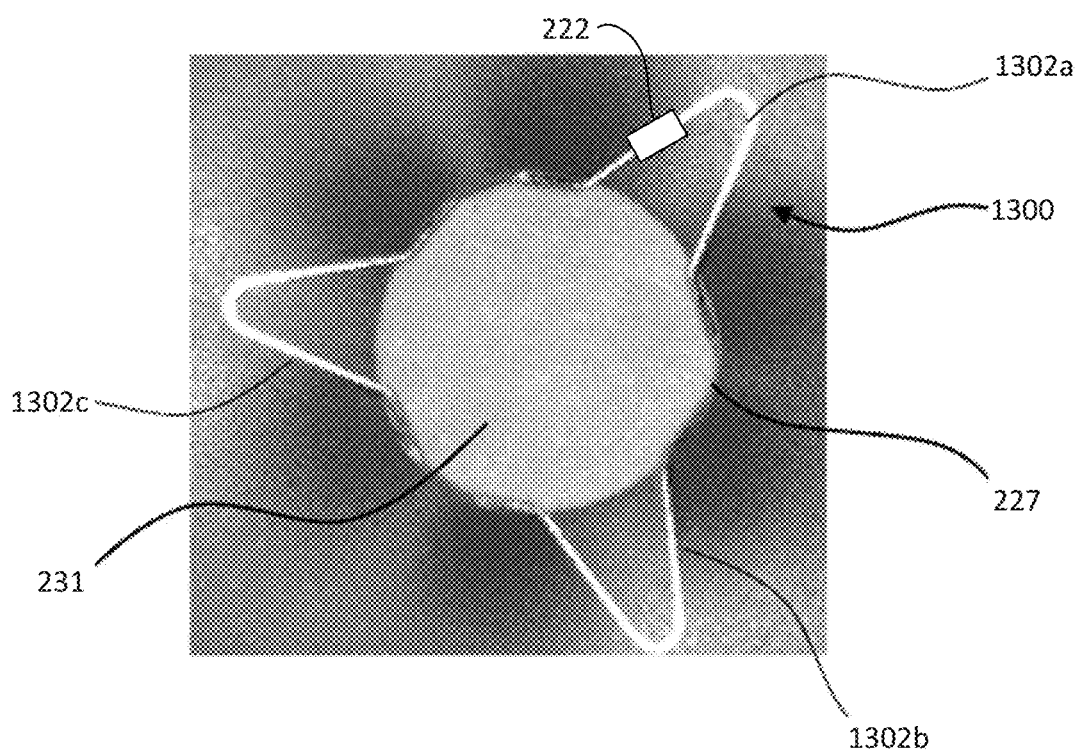
FIG. 13 shows the implantable medical device of FIG. 12 as viewed from the other side of the device.

FIG. 13 is an image of a second side of the implantable medical device 200, in accordance with an embodiment. As shown, the covering material 231 is arranged over the opening 227. In various instances, the first, second, and third lobes 1302a, 1302b, and 1302c of the second frame portion 1300 may or may not include the covering material 231. For example, as shown, the covering material 231 is arranged over the opening 27 but not over the second frame portion 1300, while in other examples, the covering material 231 may be arranged over both the opening 227 and the second frame portion 1300, for example. In some examples, the sensor assembly 224 is located on one or more of the first lobe 1302a, the second lobe 1302b, and the third lobe 1302c.

FIG. 14 shows an implantable medical device 1400 with two flanges 224 and 226 attached to a surface of the organ wall 204 according to an embodiment, where the first and second flanges are located on opposite sides of the organ wall with conduit extending through the organ wall. In one example, the organ wall 204 is an atrial wall between a left atrium and a right atrium of a heart, such that the first flange 224 is located on a surface of the atrial wall 204 in the right atrium, and the second flange is located on a surface of the atrial wall 204 in the left atrium with a conduit 1402 extending between the two flanges 224 and 226 such that the conduit 1402 forms the lumen 216 fluidly connecting the two atria of the heart.

In one example, the conduit 1402 includes a cover material, such as a membrane that has high rigidity and stiffness, for example one made of a polymer material such as fluoroelastomer, high-density polyethylene, polyethylene terephthalate (PTE), polyvinyl chloride (PVC), polyamide, polycarbonate, polymethylpentene, polypropylene, polystyrene, polysulfone, or others, in order for the membrane to exert radial force against the wall 204 to prevent the lumen 216 from collapsing.

In some examples, the conduit 1402 includes one or more structural elements (e.g., stent elements) made of a suitable material, such as shape memory alloy (e.g., a nickel-titanium alloy) or stainless steel, for example. As shown, the medical device 1400 includes a cover 1404, such as a flexible membrane of any suitable polymer material include but not limited to ePTFE. As shown, the cover 1404 is located or is otherwise configured to reside between the first flange 224 and the wall 204. Additionally, the medical device 1400 includes one or more (e.g., three) locations to place one or more sensors to perform physiological measurements within the body. In a first location 1406, a sensor (e.g., a pressure sensor) can be placed at the first flange 224 so that the sensor can perform measurements in the right atrium. In a second location 1408, a sensor (e.g., a flow sensor) can be placed inside the conduit 1402 to measure the flow of fluid within the lumen 216. In a third location 1410, a sensor (e.g., a pressure sensor) can be placed at the second flange 226 to perform measurements in the left atrium. In some examples, a single sensor performing a single sensing function is placed at each location, whereas in other examples, a plurality of sensors, or a sensor performing a plurality of sensing functions, can be placed at each location.

FIG. 15 shows the implantable medical device 1400 as shown in FIG. 14 with an additional, secondary cover 1500 (e.g., of flexible membrane material such as those previously described) according to an embodiment. In this embodiment and the embodiment shown in FIG. 14, the covers 1404 and 1500 are selectively absorptive to RF energy such that the covers are thermally opened using an RF ablation source to adjust flow through the lumen 216. In some embodiments, the covers 1404 and 1500 are selectively absorptive to laser energy such that each cover is configured to be thermally opened using a laser source. In some embodiments, the covers 1404 and 1500 are selectively absorptive to ultrasound energy such that each cover (1404 and/or 1500) is configured to be thermally opened using an ultrasound source. In some embodiments, the covers 1404 and 1500 or the elements (e.g., wires) holding the covers in place are selectively and electrolytically degradable using electrical energy supplied by an induction or other energy source.

Figure 16:
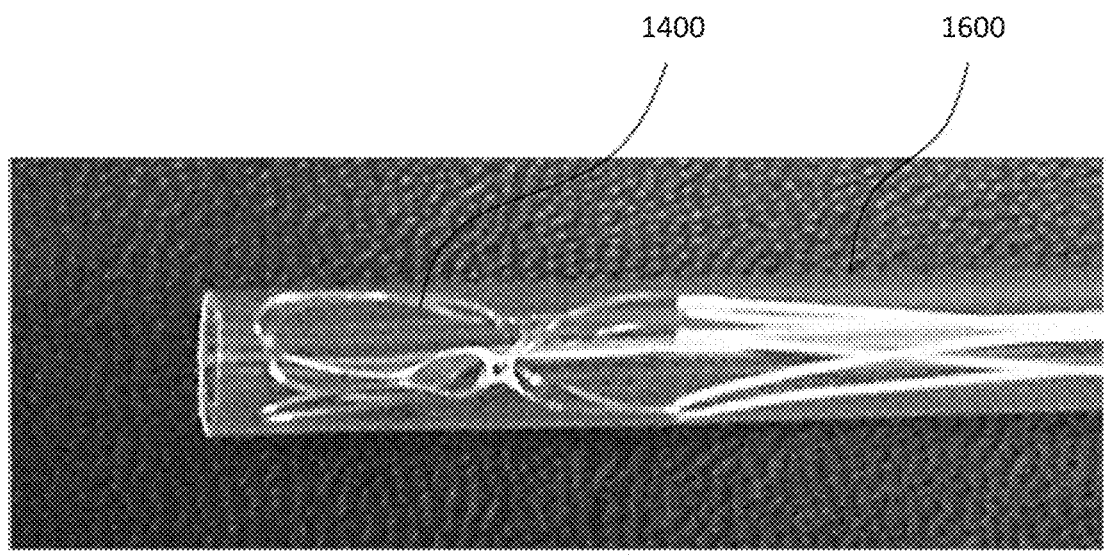
FIG. 16 shows a delivery system of an implantable medical device according to an embodiment disclosed herein.

FIG. 16 shows the implantable medical device 1400 in a compressed configuration inside a deployment apparatus 1600, in accordance with an embodiment. As shown, the device 1400 is compressed into a delivery configuration and loaded into the deployment apparatus 1600 to be delivered to a desired treatment location within the patient's body. In certain instances, the device 1400 is loaded into the deployment apparatus 1600 such that the device 1400 is completely contained within the deployment apparatus 1600, as shown in FIG. 16. The device 1400 can be delivered to the desired treatment location while in the delivery configuration. The first flange 224 is then positioned on a first side of the wall 204 and the flange 226 is positioned on a second side of the wall 204. In some instances, once deployed, the central portion or the conduit 1402 of the device 1400 can be radially expanded or compressed/restricted to adjust the rate of fluid flow through the opening as desired. In one example, the deployment apparatus 1600 includes a catheter or a sheath.

Figure 17:
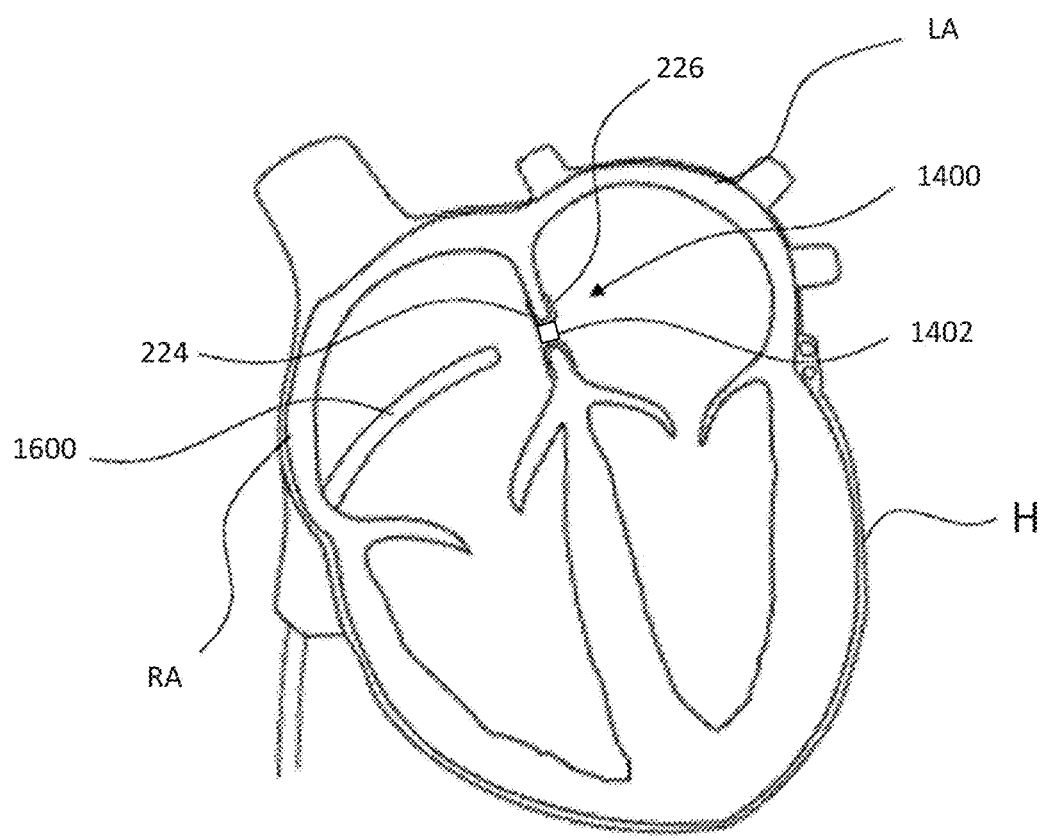
FIG. 17 shows a deployment apparatus for an implantable medical device according to an embodiment disclosed herein as the implantable medical device is delivered into a heart.

FIG. 17 shows an example of using the implantable medical device 1400 for regulating blood pressure in accordance with an embodiment. The implantable medical device 1400 is shown implanted within a heart H of a patient. The device 1400 is shown arranged between the patient's left atrium LA and right atrium RA. In certain instances, the device 1400 may be used to regulate blood flow within the heart H, for example, between the left and right atria LA, RA. As shown, the device 1400 generally includes the first flange 224 arranged on a first side of a septum (e.g., within the right atrium RA), the second flange 226 arranged on a second side of the septum (e.g., within the left atrium LA), and the conduit 1402 extending therethrough. In some examples, a needle may be used to create or open a transseptal opening in the septum.

The deployment apparatus 1600 and constraining and/or release lines (not shown) may be used to facilitate deployment of the device 1400. For example, the second flange 226 of the device 1400 may be released first after the deployment apparatus 1600 is advanced through the organ wall (e.g., septum) and into a desired internal cavity (e.g., the LA), and the first flange 224 may be released on an opposite side of the organ wall (e.g., on the RA side of the atrial septum). The conduit 1402 can be arranged within the opening in the organ wall (e.g., the trans-septal opening). The flanges 224 and 226 as well as the conduit 1402 may be compressed within the deployment apparatus 1600 during delivery of the device 1400 to the desired treatment area within the patient and subsequently expanded during deployment of the device 1400. After deployment, the device 1400 can then be used to carry out one or more treatment programs on the patient. In one example, the device 1400 detects and treats pulmonary congestion and pulmonary hypertension by taking physiologic measurements using the sensors in one or more locations within the heart. For example, if the pressure measurement within the left atrium increases with respect to the right atrium in the patient at a risk of heart failure, the sensors of the medical device 1400 detects a condition, and the conduit 1402 is opened by activating the occlusion assembly 218, for example, to allow blood flow through the lumen 216, thereby decreasing the pressure within the left atrium to a safe level.

Figure 18:
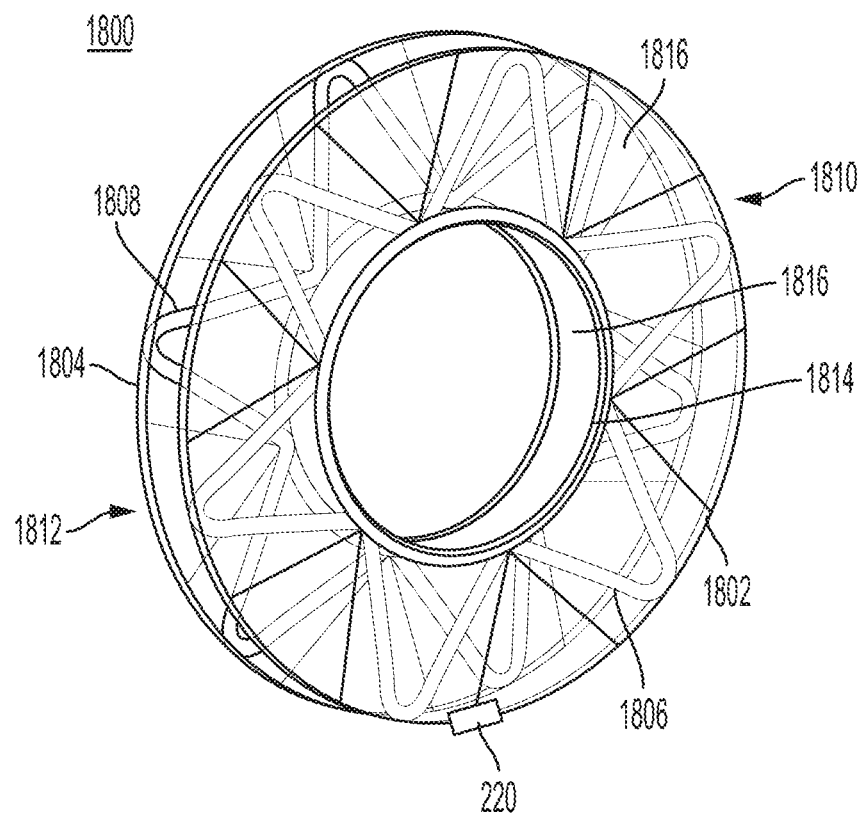
FIG. 18 shows an implantable medical device according to an embodiment disclosed herein as viewed from one side of the device.

FIG. 18 shows an example of an implantable medical device 1800 for regulating blood pressure in accordance with an embodiment. As shown, the implantable medical device 1800 includes the first frame component 1802 and the second frame component 1804. The first frame component 1802 may be configured to conform to the patient's anatomy (i.e., the first side of the septum, for example). The second frame component 1804 may be configured to conform to the patient's anatomy (i.e., the second side of the septum). In some examples, the sensor assembly 220 is located on one or both of the first frame component 1802 and the second frame component 1804.

In certain instances, the first frame component 1802 includes a first set of elongate elements 1806, and the second frame component 1804 includes a second set of elongate elements 1808. The frame components 1802, 1804, including and for example the elongate elements 1806, 1808, may be discrete and separate from one another. For example, the first frame component 1802 forms a first side 1810 of the device 1800 and the second frame component 1804 forms a second side 1812 of the device 1800. The first frame component 1802 being discrete and separate from the second frame component 1804 does not enter into the second side 1812 of the device and the second frame component 1804 being discrete and separate from the first frame component 1802 does not enter into the first side 1810 of the device.

In certain instances, the first and second frame components 1802, 1804 are non-contiguous with one another. The first and second frame components 1802, 1804 being non-contiguous with one another allows the first and second frame components 1802, 1804 to be distinct and separate from one another. In addition, the first and second frame components 1802, 1804 are free to move, in response to movement of the patient's anatomy, separate from one another. In this manner, forces acting on one of the first and second frame components 1802, 1804 are maintained within the other of the first and second frame components 1802, 1804. The forces acting on one of the first and second frame components 1802, 1804 may be isolated to the frame component to which the force is acted on.

As shown, the conduit portion 1814 is arranged between the first frame component and the second frame component. At least a portion of the conduit portion 1814 is generally radially or circumferentially unsupported by the first and second frame components 1802, 1804 within the conduit portion 1814. As shown in FIG. 18, the conduit portion 1814 transitions to the first side 1810 and the second side 1812 at approximately a 90 degree angle (other angles are contemplated). Bounds of the conduit portion 1814 may be considered to be a location at which the conduit portion 1814 transitions to the first side 1810 and the second side 1812. The first and second frame components 1802, 1804 extend laterally relative to the conduit portion 1814. In addition, the first and second frame components 1802, 1804 may support the conduit portion 1814 without substantially entering the bounds of the conduit portion 1814. In certain instances, the first and second frame components 1802, 1804 support the conduit portion 1814 laterally from outside of bounds the conduit portion 1814. Thus, the first and second frame components 1802, 1804 may maintain a lumen through the conduit portion 1814 and facilitate deployment of the conduit portion 1814 by laterally forcing the conduit portion 1814 open.

In certain instances, the first and second frame components 1802, 1804 may impart tension to the conduit portion 1814 to deploy and maintain the conduit portion 1814 with a lumen therethrough. The conduit portion 1814 may be deployed within the septum between tissue surfaces through an opening (e.g., needle stick across the septum) that has a diameter smaller than a fully deployed diameter of the conduit portion 1814. Tension in the conduit portion 1814 imparted by expansion of the first and second frame components 1802, 1804 may also expand the septum between tissue surfaces to a desired shunt size.

In certain instances, the conduit portion 1814 may be substantially free of frame components. For example, because the first and second frame components 1802, 1804 are non-contiguous with one another, as described above, and are arranged external to the bounds of the conduit portion 1814. The conduit portion 1814 may include, for example, a membrane 1816, such as an expanded polytetrafluoroethylene (ePTFE) membrane, connecting the first frame component 1802 and the second frame component 1804. The membrane 1816 generally separates the first frame component 1802 and the second frame component 1804 by a suitable distance compatible with the patient's body. For example, the membrane 1816 can separate the first frame component 1802 and the second frame component 1804 by a gap of from 0 to 15 mm depending on the desired treatment location within the patient's body. In addition, the conduit portion may be formed of only the membrane 1816. The conduit portion 1814, which is configured to be deployed within the septum between tissue surfaces, is free of the first frame component 1802 and the second frame component 1804. The conduit portion 1814 may include a smooth interior that facilitates blood flow therethrough without ridges from a stent element interrupting or disrupting flow. Thus, the conduit portion 1814 may lessen the opportunity for thrombosis.

In addition to the membrane 1816 forming the conduit portion 1814, the membrane 1816 may also cover at least a portion of the first frame component 1802, at least a portion of the second frame component 1804, or at least a portion of the first frame component 1802 and the second frame component 1804. In certain instances, the membrane 1816 arranged on at least a portion of the first frame component 1802 and/or the second frame component 1804 is a separate membrane film (e.g., a first membrane film arranged on first frame component 1802 and a second membrane film arranged on the second frame component 1804). In these instances, the membrane film or films may be coupled to the membrane 1816 in the conduit portion 1814. The membrane 1816 may be elastic to allow for expansion of the conduit portion 1814 and to allow for movement of portions of the first frame component 1802 and/or the second frame component 1804 (e.g., movement of the first set of elongate elements 1806 and/or the second set of elongate elements 1808).

The membrane 1816 may span gaps between the first set of elongate elements 1806 and/or the second set of elongate elements 1808. The membrane 1816, in certain instances, is arranged on at least a tissue engaging side of the first frame component 1802 and a tissue engaging side the second frame component 1804. In these instances, the membrane 1816 is configured to lessens frame erosion potential of the first frame component 1802 and/or the second frame component 1804. The membrane 1816 and the arrangement of the first set of elongate elements 1806 and/or the second set of elongate elements 1808 may conform to the tissue surfaces surrounding the septum. The first set of elongate elements 1806 and/or the second set of elongate elements 1808 may lay flat against the tissue surfaces.

In certain instances, each of the first set of elongate elements 1806 may be attached to one another via the membrane 1816 to form the first frame component 1802. In certain instances, the first frame component 1802 may form a substantially flat or 2-dimensional, disc-like shape, as shown. Additionally, or alternatively, the second set of elongate elements 1808 may also be attached to one another via the membrane material 1816 to form the second frame component 1804. The second frame component 1804 may also form a substantially flat or 2-dimensional, disc-like shape such that the first and second frame components 1802, 1804 are substantially parallel to one another when the device 1800 is in a deployed configuration.

In certain instances, the membrane 1816 may be configured to promote or inhibit tissue ingrowth over at least a portion of the membrane 1816, or at least a portion of the membrane 1816. In certain instances, the membrane 1816 is configured to promote or inhibit tissue ingrowth to cover at least a portion of the first and/or second frame components 1802, 1804, which may further promote compatibility and stability of the device 1800 within the patient's body. The membrane 1816 within the conduit portion 1814 may be configured to not allow tissue ingrowth leading to increased patency. In certain instances, the membrane 1816 is configured to promote endothelization without obstructive ingrowth within the conduit portion 1814. The membrane 1816 may promote endothelization without obstructive overgrowth of tissue into the conduit portion 1814.

In certain instances, the device 1800 may be capable of delivering a drug to the desired treatment location within the patient's body. For example, the device 1800 may be capable of eluting a drug configured to modulate tissue response. In certain instances, the device 1800 may be coated with a therapeutic coating, drug eluting material or other therapeutic material or a hydrophilic coating. In one specific example, the device 1800 can be coated with heparin to facilitate thromboresistance and patency of the device 1800. Alternatively, or additionally, the device 1800 may include paclitaxel (to modulate tissue/cellular response).

Figure 19:
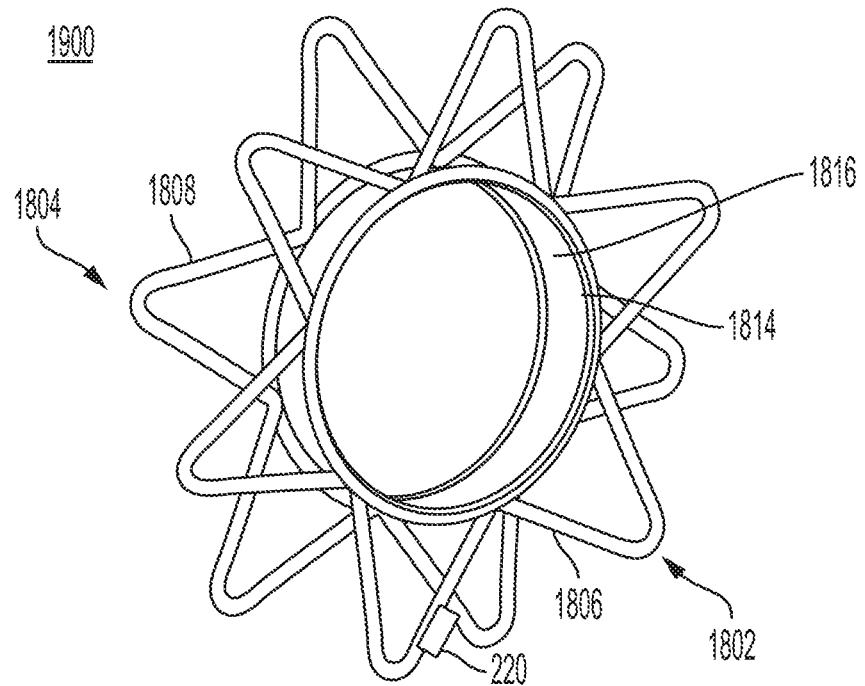
FIG. 19 shows an implantable medical device according to an embodiment disclosed herein as viewed from one side of the device.

FIG. 19 is a perspective view of another example of an implantable medical device 1900 for regulating blood pressure in accordance with an embodiment. As shown, each of the first set of elongate elements 1806 may be discrete and separate from adjacent elongate elements. In other terms, the membrane 1816 does not connect each of the first set of elongate elements 1806 together. In this way, each of the first set of elongate elements 1806 may move independently from one another and individually conform to the topography of the first side of the septum, thus providing a highly conformable first frame component 1802. Each of the second set of elongate elements 1808 may also be discrete and separate from adjacent elongate elements. For example, each of the second set of elongate elements 1808 may move independently from one another and individually conform to the second side of the septum, much like the first set of elongate elements 1806 conforms to the first side of the septum. Thus, both the first and second frame components 1802, 1804 are highly conformable and may conform independently of one another based on the patient's anatomy.

In certain instances, one of the first or second set of elongate elements 1806, 1808 of the first and second frame components 1802, 1804 may be attached to one another via the membrane 1816 while the other set of elongate elements are unattached (e.g., they are discrete and separate from adjacent elongate elements). In other instances, only some of the first or second set of elongate elements 1806, 1808 may be attached to one another, while other elongate elements of the first and second set of elongate elements 1806, 1808 are not attached. Thus, the device 1900 can be highly customizable to the patient depending on the desired treatment location within the patient, and size and/or shape of the defect, among other factors. In some examples, the sensor assembly 220 is located on one or both of the first frame component 1802 and the second frame component 1804.

The device 1900 is generally deployable or expandable from a delivery configuration to the deployed configuration. In some instances, the first set of elongate elements 1806 and the second set of elongate elements 1808 may nest within one another when the device is in the delivery configuration. This allows the device 1900 to compress to a smaller size, for example, for delivery of the device 1900 to a wider variety of treatment locations (e.g., through small, narrow, or convoluted passageways).

Figure 20:
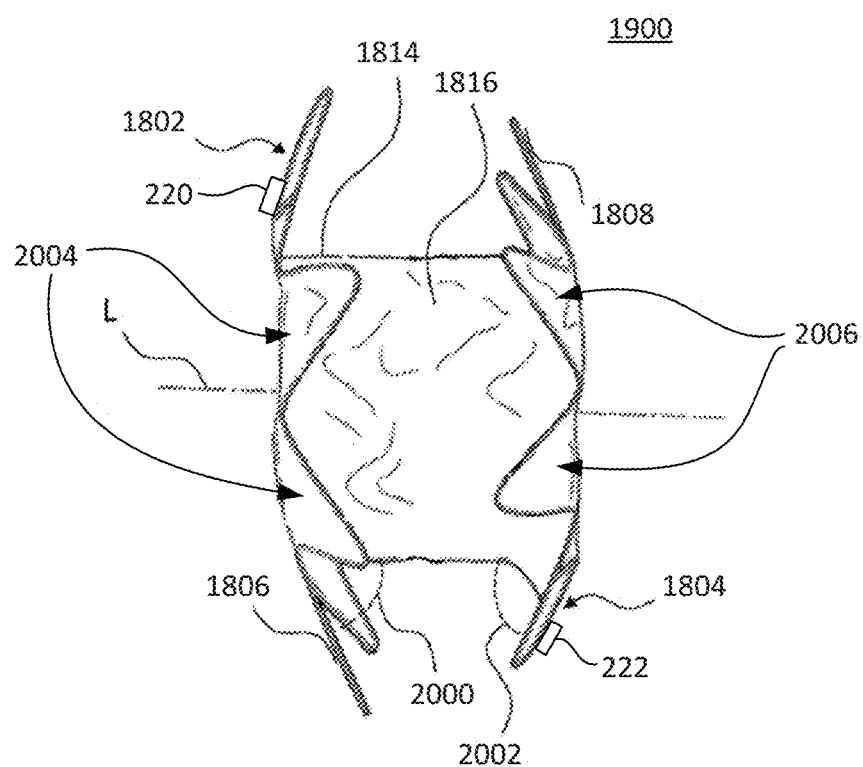
FIG. 20 shows an implantable medical device according to an embodiment disclosed herein as viewed from one side of the device.

FIG. 20 is a side view of the implantable medical device 1900 for regulating blood pressure, shown in FIG. 19, in accordance with an embodiment. FIG. 20 shows the device 1900 in the deployed configuration. As shown, the first frame component 1802 including the first set of elongate elements 1806 and the second frame component 1804 including the second set of elongate elements 1808 are positioned radially outward with respect to a longitudinal axis L of the conduit portion 1814 when the device 1900 is in the deployed configuration. For example, the first and second frame components 1802, 1804 are positioned at first and second angles 2000, 2002, respectively. The first and second angles 2000, 2002 may form approximately a 90° angle with respect to the longitudinal axis L when the device is in the deployed configuration. This allows the first and second frame components 1802, 1804 to be positioned parallel with and adjacent to the first and second sides of the septum. In certain instances, the first and second frame components 1802, 1804 may be positioned at any angle relative to the longitudinal axis L (for example, from about 0° to greater than 90° with respect to the longitudinal axis L) that allows for contact with the tissue surface of the first and second sides of the septum.

In certain instances, the first and second elongate elements 1806, 1808 are configured to separate from one another when the device 1900 is in the deployed configuration. As shown in FIG. 20, each of the first set of elongate elements 1806 are discrete and separate from one another when the device 1900 is in the deployed configuration such that each of the first set of elongate elements 1806 may move independently from adjacent elongate elements. Each of the second set of elongate elements 1808 may also be discrete and separate from one another when the device 1900 is in the deployed configuration such that each of the second set of elongate elements 1808 move independently from adjacent elongate elements. In some examples, the sensor assembly 220 may be located on any one or more of the first set of elongate elements 1806, and the other sensor assembly 222 may be located on any one or more of the second set of elongate elements 1808.

The first and second frame components 1802, 1804 may maintain a lumen through the conduit portion 1814 and facilitate deployment of the conduit portion 1814 by laterally forcing the conduit portion 1814 open. In addition, the lumen may be free or without the first and second frame components 1802, 1804. In this manner, the conduit portion 1814 may facilitate re-crossing of the septum for addition procedures (e.g., left atrial appendage occluder implantation). In addition, the first and second frame components 1802, 1804 may be differently configured. For example, one of the first and second frame components 1802, 1804 may be flared while the other of the first and second frame components 1802, 1804 is flat. In other instances, both the first and second frame components 1802, 1804 may be flared. In addition, one of the first and second frame components 1802, 1804 may be convex while the other of the first and second frame components 1802, 1804 is flat or concave or both the first and second frame components 1802, 1804 may be convex. Further, one of the first and second frame components 1802, 1804 may be concave while the other of the first and second frame components 1802, 1804 is flat or convex or both the first and second frame components 1802, 1804 may be concave. In addition, the first and second frame components 1802, 1804 may be different sizes.

The first and second frame components 1802, 1804 may include a sensor integrated into the respective frame component, for example, for continuous monitoring of various hemodynamic parameters such as pressure, among other parameters, within the patient's body. For example, an antenna or inductor may be wrapped around the perimeter of one of the first and second frame components 1802, 1804 and the sensor may be attached to the inductor. The sensor may be configured to, for example, sense physiologic properties, such as temperature, electrical signals of the heart, blood chemistry, blood pH level, hemodynamics, biomarkers, sound, pressure, and electrolytes that may be important in diagnosing, monitoring, and/or treating heart disease, heart failure, and/or other cardiovascular disease states In certain instances, the conduit portion 1814 may be sizeable after delivery. The membrane 1816 may be selectively adjustable by a balloon applied within the conduit portion 1814 to distend the membrane 1816. The device 1900 can be any size suitable to fit the anatomy of the patient. In certain instances, a diameter of the conduit portion is from 3 to 12 mm. For example, the diameter of the conduit portion may be from 4 to 10 mm, or from 5 to 8 mm depending on the anatomy of the patient and/or the desired treatment location. The first and second frame components 1802, 1804 generally have a larger diameter than that of the conduit portion 1814, for example, so that the frame components may anchor the conduit portion 1814 of the device 1900 within the septum.

The device 1900 can be any shape suitable to fit the anatomy of the patient. For example, the first and second frame portions 1802, 1804 may be any of a variety of suitable shapes for anchoring the device 1900 within the patient's body. For example, the first and second frame portions 1802, 1804 may be substantially circular, ovular, diamond-shaped, star-shaped, flower-shaped, or any other suitable shape as desired. In certain instances, for example, at least one of the first and second set of elongate elements 1806, 1808 form a star shape. In certain instances, both the first and second set of elongate elements 1806, 1808 form a star shape.

In certain instances, the first set of elongate elements 1806 forms a plurality of first lobes 2004 and the second set of elongate elements 1808 forms a plurality of second lobes 2006. Each of the plurality of first and second lobes 2004, 2006 may include, for example, from 3 to 12 lobes, from 4 to 10 lobes, or from 6 to 8 lobes as desired. In certain instances, the plurality of first lobes 2004 may have more lobes than the plurality of second lobes 2006, while in other instances, the plurality of first lobes 2004 may have the same number of lobes or less lobes than the plurality of second lobes 2006.

Figure 21:
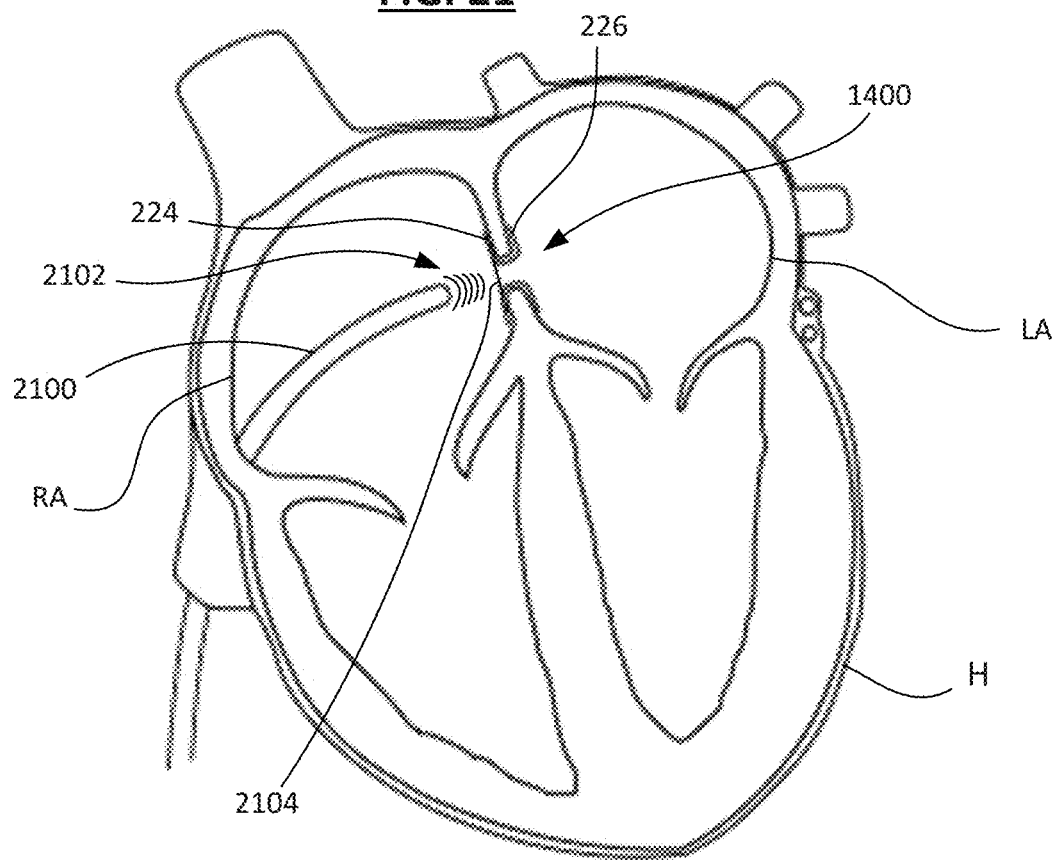
FIG. 21 shows an energization unit for an implantable medical device according to an embodiment disclosed herein as viewed from one side of the device.

FIG. 21 shows an example of an implantable medical device 1400 being activated by an energy source, for example an energization unit 2100, in accordance with an embodiment. The energization unit 2100 functions in a way similar to the extracorporeal energization unit 800 in that the energization unit 2100 can transmit energy to the implantable medical device via magnetic induction and this energy can be converted to electrical energy to electrolytically degrade an element of the implanted medical device. Alternately, the energization unit 2100 can deliver energy via an ultrasonic energy source, a laser energy source, a radiofrequency (RF) energy source, and/or another type of suitable energy source, which applies an energy transfer 2102 to form an aperture in a membrane coupled to a flange, for example a membrane 2104 coupled to the first flange 224. Unlike the extracorporeal energization unit 800, the energization unit 2100 is delivered to a location within the heart H (e.g., in the right atrium RA) that is proximate to the membrane 2104. In one embodiment, a membrane of the membrane 2104 can be melted to form the aperture after exposing the membrane 2104 to thermal or ultrasound energy, to produce a thermal activation mechanism. In some examples, the size of the aperture can be adjusted by varying the amount of thermal activation.

In some embodiments, the medical device 1400 may include an additional, secondary membrane (not shown) coupled to the second flange 226. In these embodiments, one or both of the membranes are selectively absorptive to ultrasound such that the membranes are configured to be thermally opened using an ultrasound source to adjust flow through the medical device 1400. In some embodiments, one or both of the membranes are selectively absorptive to RF energy such that the membranes are thermally opened using an RF ablation source to adjust flow through the medical device 1400. In some embodiments, the membrane is selectively absorptive to laser energy such that the membrane is configured to be thermally opened using a laser source. In some embodiments, the membrane or the elements (e.g., wires) holding the membrane in place are selectively and electrolytically degradable using electrical energy supplied by an induction or other energy source. In some embodiments, both membranes are actuatable utilizing similar methods. For example, the membranes can both be configured to open simultaneously in response to receiving energy from an external source, e.g. RF energy, laser energy, induction energy, or others.

In some embodiments, one or both of the membranes are under radial tension to assist with forming one or both of the apertures therethrough. For example, when the membrane(s) are stretched, even a small opening in the membrane(s) can be enlarged when the radial tension placed from the outer edge of the membrane(s) pull the membrane(s) away from the locations of the openings in a plurality of directions. In some embodiments, the membrane(s) exhibit residual stress profile to assist with forming the one or both of the apertures in the membrane(s). In some embodiments, the membrane(s) are selectively openable between a plurality of sizes for the one or both of the apertures to modify flow through the medical device 1400.

FIG. 22 shows an example of an implantable medical device 2200 according to an embodiment. The implantable medical device 2200 has two flanges 224 and 226 engaged with a surface of the organ wall 204 to secure the medical device 2200 in place, where the flanges 224 and 226 are located on opposite sides of the organ wall 204. In one example, the organ wall 204 is an atrial wall between a left atrium and a right atrium of a heart, such that the first flange 224 is located on a surface of the atrial wall 204 in the right atrium, and the second flange is located on a surface of the atrial wall 204 in the left atrium with a conduit 1402 extending between the two flanges 224 and 226 such that the conduit 1402 forms the lumen 216 fluidly connecting the two atria of the heart. In other examples, the medical device 2200 is secured to a ventricular wall or other tissue of the body as desired.

In some examples, the conduit 1402 includes a membrane 2202 made of a polymer material as described above that is impermeable to blood under physiologic conditions such that the membrane 2202 separates the lumen 216 into two sections: a first lumen section 216A and a second lumen section 216B. In some examples, the membrane 2202 is positioned in the middle of the lumen 216, though the membrane may be offset toward or located at either end of the lumen 216. In some examples, the membrane 2202 is positioned at any location in the lumen 216 such that the first lumen section 216A has a greater volume than the second lumen section 216B or vice versa.

The membrane 2202 helps prevent fluid flow through the lumen 26 (e.g., between the first and second lumen sections 216A and 216B), and therefore between the two opposite sides of the organ wall 204. In some examples, the membrane 2202 can be selectively absorptive to ultrasound, RF energy, laser energy, or any suitable source of energy as previously described, in which case absorbing the energy causes the membrane 2202 to degrade, melt, or open to allow fluid to flow between the first and second lumen sections 216A and 216B. In some examples, the amount of fluid flow can be adjusted by changing a degree of degradation or a size of the opening in the membrane 2202.

Additionally, the medical device 2200 includes one or more (e.g., three) locations to place one or more sensors to perform physiological measurements within the body. The first location 1406 and the third location 1410 are essentially similar to those mentioned above with respect to the medical device 1400. The second location 1408 can be inside the conduit 1402 for the sensor (e.g. a flow sensor) to measure the flow of fluid within the lumen 216. In some examples, the second location 1408 can be located in the first lumen section 216A or the second lumen section 216B. In some examples, the second location 1408 can be adjacent to or proximate to the membrane 2202 such that the sensor would also be able to detect when the membrane 2202 is opened or degraded to permit fluid flow through the lumen 216.

Although various examples have been provided in the context of a trans-septal approach with the device located between two atria, it should be understood that a variety of different applications and locations are contemplated (e.g., trans-septal between ventricles, between an aorta and heart chamber, between two blood vessels, between two GI organs, or others. In other words, the invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device, comprising:
a fluid shunt adapted to extend through a wall separating a first cavity and a second cavity within the heart, the fluid shunt including a first portion adapted to extend into the first cavity within the heart, a second portion adapted to extend into the second cavity within the heart, and an intermediate portion interconnecting the first and second portions, the fluid shunt having a lumen extending between the first and second portions that is adapted to fluidly couple the first and second cavities within the heart;
an occlusion assembly associated with the fluid shunt and adapted to selectively occlude flow through the lumen of the fluid shunt, the occlusion assembly being configured to be in a closed configuration such that the lumen of the fluid shunt is initially in a sealed state and to be thermally activated to adjust flow through the lumen of the fluid shunt, wherein the occlusion assembly comprises a thermoplastic polymer membrane cover that is impermeable to blood under physiologic conditions and configured to be activated by heating to adjust flow through the lumen of the fluid shunt; and
at least one sensor assembly associated with the first portion of the fluid shunt such that the at least one sensor assembly is adapted to sense one or more physiologic parameters in the first cavity.

2. The implantable medical device of claim 1, wherein the at least one sensor assembly comprises a first sensor assembly and a second sensor assembly associated with the second portion of the fluid shunt such that the second sensor assembly is adapted to sense one or more physiologic parameters in the second cavity.

3. The implantable medical device of claim 1, further comprising a control unit in communication with the at least one sensor assembly the control unit comprising:
a receiver coupled to the at least one sensor assembly, the receiver configured to receive physiologic parameter information from the at least one sensor assembly; and
a processing unit coupled to the receiver for analyzing the physiologic parameter information received by the receiver.

4. The implantable medical device of claim 3, further comprising a thermal actuation mechanism associated with the occlusion assembly, the control unit being operatively coupled to the thermal actuation mechanism and configured to send a control signal to activate the thermal actuation mechanism in response to the analysis of the physiologic parameter.

5. The implantable medical device of claim 4, wherein the at least one sensor assembly is operably coupled to the thermal actuation mechanism of the occlusion assembly such that upon the at least one sensor assembly sensing a predetermined physiologic measurement, the thermal actuation mechanism is adapted to increase flow through the lumen of the fluid shunt.

6. The implantable medical device of claim 1, wherein at least one of the first and second portions of the fluid shunt includes a flange member for engaging the wall of the heart.

7. The implantable medical device of claim 1, wherein the fluid shunt includes a support.

8. The implantable medical device of claim 7, wherein the support includes a resilient framework.

9. The implantable medical device of claim 1, wherein the cover includes a composite membrane material.

10. The implantable medical device of claim 1, wherein the first cavity is a left atrium of the heart and the second cavity is a right atrium of the heart.

11. The implantable medical device of claim 1, wherein the cover is configured to be selectively absorptive to ultrasound such that the membrane is configured to be thermally opened using an ultrasound source to adjust flow through the lumen of the fluid shunt.

12. The implantable medical device of claim 1, wherein the cover is configured to be selectively absorptive to laser energy such that the membrane is configured to be thermally opened using a laser source.

13. The implantable medical device of claim 1, wherein the cover is configured to be selectively absorptive to radiofrequency energy such that the cover is configured to be thermally opened using a radiofrequency energy source.

14. The implantable medical device of claim 1, wherein the cover is configured to cover the first portion of the fluid shunt that is adapted to extend into the first cavity within the heart.

15. The implantable medical device of claim 14, further comprising a secondary cover, wherein the secondary cover is configured to cover the second portion of the fluid shunt that is adapted to extend into the second cavity within the heart.

16. The implantable medical device of claim 1, wherein the fluid shunt includes a membrane disposed in the lumen between the first and second portions that is impermeable to blood under physiologic conditions.

17. The implantable medical device of claim 1, wherein the device is part of a system including at least one of an extracorporeal induction energy source, an internal induction energy receiver, an ultrasonic energy source, a laser energy source, an RF energy source or another type of energy source for activating the occlusion assembly.

18. The implantable medical device of claim 1, wherein the device is configured to exhibit different resonant frequencies based upon a flow rate through the lumen of the fluid shunt.

19. A medical treatment system comprising:
an implantable medical device comprising:
a fluid shunt adapted to extend through a wall separating a first cavity and a second cavity within the heart, the fluid shunt including a first portion adapted to extend into the first cavity within the heart, a second portion adapted to extend into the second cavity within the heart, and an intermediate portion interconnecting the first and second portions, the fluid shunt having a lumen extending between the first and second portions that is adapted to fluidly couple the first and second cavities within the heart;
an occlusion assembly associated with the fluid shunt and adapted to selectively occlude flow through the lumen of the fluid shunt, the occlusion assembly being configured to be in a closed configuration such that the lumen of the fluid shunt is initially in a sealed state and to be thermally activated to adjust flow through the lumen of the fluid shunt, wherein the occlusion assembly comprises a thermoplastic polymer membrane cover that is impermeable to blood under physiologic conditions and configured to be activated by heating to adjust flow through the lumen of the fluid shunt; and
at least one sensor assembly associated with the first portion of the fluid shunt such that the at least one sensor assembly is adapted to sense one or more physiologic parameters in the first cavity; and
a deployment catheter configured to compress the implantable medical device and maintain the implantable medical device in a compressed configuration until the implantable medical device is deployed at a desired treatment location within the heart.

\* \* \* \* \*